United States Patent
Bacallao et al.

(10) Patent No.: US 11,911,487 B2
(45) Date of Patent: Feb. 27, 2024

(54) HYDRODYNAMIC METHODS FOR DELIVERING FLUIDS TO KIDNEY TISSUES AND RELATED MATERIALS AND METHODS

(71) Applicants: Indiana University Research & Technology Corporation, Indianapolis, IN (US); United States Government as Represented by the Department of Veterans Affairs, Washington, DC (US)

(72) Inventors: Robert Bacallao, Indianapolis, IN (US); Simon Atkinson, Carmel, IN (US); George Rhodes, Fishers, IN (US); Peter Corridon, Indianapolis, IN (US)

(73) Assignees: Indiana University Research and Technology Corporation, Bloomington, IN (US); United States Government as Represented by the Department of Veterans Affairs, Washington, DC (US)

( * ) Notice: Subject to any disclaimer, the term of this patent is extended or adjusted under 35 U.S.C. 154(b) by 165 days.

(21) Appl. No.: 14/398,697

(22) PCT Filed: May 3, 2013

(86) PCT No.: PCT/US2013/039454
§ 371 (c)(1),
(2) Date: Nov. 3, 2014

(87) PCT Pub. No.: WO2013/166378
PCT Pub. Date: Nov. 7, 2013

(65) Prior Publication Data
US 2016/0324988 A1 Nov. 10, 2016

Related U.S. Application Data

(60) Provisional application No. 61/770,848, filed on Feb. 28, 2013, provisional application No. 61/680,757, filed on Aug. 8, 2012, provisional application No. 61/642,203, filed on May 3, 2012.

(51) Int. Cl.
| | | |
|---|---|---|
| *A61K 33/00* | (2006.01) | |
| *A61K 48/00* | (2006.01) | |
| *A61K 9/00* | (2006.01) | |
| *A61K 38/44* | (2006.01) | |
| *A61K 38/45* | (2006.01) | |
| *C12N 7/00* | (2006.01) | |

(52) U.S. Cl.
CPC ........ *A61K 48/0075* (2013.01); *A61K 9/0019* (2013.01); *A61K 38/443* (2013.01); *A61K 38/45* (2013.01); *A61K 48/0058* (2013.01); *C12N 7/00* (2013.01); *C12Y 101/01042* (2013.01); *C12Y 208/02* (2013.01); *C12N 2710/10041* (2013.01)

(58) Field of Classification Search
None
See application file for complete search history.

(56) References Cited

U.S. PATENT DOCUMENTS

| | | | |
|---|---|---|---|
| 4,954,129 A * | 9/1990 | Giuliani | A61M 25/0017 604/131 |
| 5,328,471 A | 7/1994 | Slepian | |
| 6,699,231 B1 | 3/2004 | Sterman et al. | |
| 6,784,154 B2 * | 8/2004 | Westenfelder | A61K 38/1816 514/1.4 |
| 2002/0102241 A1 | 8/2002 | Arnaout et al. | |
| 2003/0064953 A1 | 4/2003 | Liu et al. | |
| 2003/0170897 A1 | 9/2003 | Imai et al. | |
| 2005/0238648 A1 | 10/2005 | Jacobs et al. | |
| 2008/0269150 A1 | 10/2008 | Fischer | |
| 2008/0300571 A1 | 12/2008 | LePivert | |
| 2009/0042738 A1 | 2/2009 | Moore | |
| 2009/0105173 A1* | 4/2009 | Feinstein | A61K 31/70 514/44 R |
| 2010/0113939 A1 | 5/2010 | Mashimo | |
| 2016/0213896 A1 | 7/2016 | Bacallao | |
| 2016/0324988 A1 | 11/2016 | Atkinson et al. | |

FOREIGN PATENT DOCUMENTS

| | | | |
|---|---|---|---|
| WO | WO 2004/001049 A1 | 12/2003 | |
| WO | WO 2007/061530 A1 | 5/2007 | |
| WO | WO 2007084342 A2 | 7/2007 | |
| WO | WO 2010/062778 A2 | 6/2010 | |
| WO | WO 2013119880 A1 | 8/2013 | |

OTHER PUBLICATIONS

Mayo Clinic Definition, 2015.*
Singh et al., Pharmacological Reports, 2012, 64: 31-44.*
Molitoris et al., Advanced Drug Delivery Reviews, 2006, 58: 809-823.*
Baliga et al., American Journal of Kidney Diseases, 1997, 29: 465-477.*
Jo et al., J. Biol. Chem., 2001, 276: 16168-16176.*
Krawczeski et al., Journal of the American College of Cardiology, 2011, 58: 2301-2309.*
Vesey et al., Nephrol. Dial. Transplant., 2004, 19: 348-355.*
Devarajan , J. Am. Soc. Nephrol., 2006, 17: 1503-1520.*

(Continued)

*Primary Examiner* — Ileana Popa
(74) *Attorney, Agent, or Firm* — Faegre Drinker Biddle & Reath LLP

(57) ABSTRACT

The present invention provides methods and materials useful delivering liquids, including liquids comprising nucleic acid molecules into cells. In particular, the present invention provides methods for delivering saline solution, exogenous compositions, and isolated vectors to kidney cells, using the renal vein as a guide and under hydrodynamic pressure. The delivery methods and materials herein are useful to research, prognose, ameliorate symptoms of kidney injury, and treat kidney pathologies.

12 Claims, 24 Drawing Sheets
(21 of 24 Drawing Sheet(s) Filed in Color)

(56) References Cited

OTHER PUBLICATIONS

Maruyama et al., J. Biochem., 2005, 137: 373-380.*
Johnson et al., Kidney International, 2006, 69: 1806-1813.*
Nakamura et al., Mol. Biotechnol., 2008, 38: 109-119.*
Sutton et al., Kidney Int., 2002, 62: 1539-1549.*
Hellberg et al., Kidney Int., 1990, 37: 1240-1247.*
Maruyama et al., Human Gene Therapy, 2002, 13: 455-468.*
LeDuc et al., Journal of Emergency Nursing, 1997, 23: 306-309.*
Mason, Kidney Int., 1987, 31: 65-71.*
Raininko et al., Acta Radiologica, 1990, 31, 3: 309-314.*
Ho et al., Am. J. Kidney Dis., 2012, 59: 196-201.*
PCT International Search Report and Written Opinion, Application No. PCT/US2013/039,454, dated Sep. 18, 2013.
International Preliminary Report on Patentability issued by The International Bureau of WIPO, dated Sep. 4, 2014, for International Application No. PCT/US2013/039454; 10 pages.
European Search Report issued by the European Patent Office, dated Jan. 21, 2016, for related application No. EP 13784903; 7 pages.
International Search Report and Written Opinion issued by the ISA/US, Commissioner for Patents, dated Dec. 4, 2014, for related International Application No. PCT/US2014/053681; 7 pages.
International Preliminary Report on Patentability issued by The International Bureau of WIPO, Mar. 1, 2016, for International Application No. PCT/US2014/053681; 6 pages.
Extended European Search Report issued by the European Patent Office, Munich, Germany, dated Mar. 27, 2017, for European Patent Application No. 14840753.9; 7 pages.
Office Action and Examination Search Report issued by the Canadian Intellectual Property Office dated Nov. 29, 2019 for Canadian Patent Applicaiton No. 2,874,316; 4 pages.
Office Action and Examination Search Report issued by the Canadian Intellectual Property Office dated Nov. 23, 2018 for Canadian Patent Applicaiton No. 2,874,316; 4 pages.
Communication Pursuant to Article 94(3) issued by the European Patent Office, dated Mar. 14, 2019, for European Patent Application No. 13784903.0; 3 pages.
European Search Report and Search Opinion issued by the European Patent Office, dated Feb. 11, 2016, for European Patent Application No. 13784903.0; 7 pages.

* cited by examiner

HYDRODYNAMIC METHODS FOR DELIVERING FLUIDS TO KIDNEY TISSUES AND RELATED MATERIALS AND METHODS

CROSS REFERENCE TO RELATED APPLICATIONS

This application claims the priority benefit of U.S. Provisional Application No. 61/642,203, filed May 3, 2012; and U.S. Provisional Application No. 61/680,757, filed Aug. 8, 2012; and U.S. Provisional Application No. 61/770,848, filed Feb. 28, 2013.

STATEMENT REGARDING FEDERALLY SPONSORED RESEARCH

This invention was made with government support under DK053194, DK088934, and DK079312 awarded by the National Institutes of Health. The Government has certain rights in the invention.

BACKGROUND OF THE INVENTION

Reliable methods for gene transfer to specific target cells in live animals have the potential both to enhance basic and disease-focused research in animal models and to facilitate the advancement of gene therapy in humans. Numerous methods have been proposed to deliver exogenous genes to mammalian cells in situ. These techniques could provide inexpensive and rapid alternatives to pronuclear microinjection-derived transgenic models. However, more efficient approaches are needed to enhance gene transfer by improving the distribution, extent and duration of gene expression, while minimizing injury associated with the delivery.

Generally, in vivo nucleic acid molecule transfer rates are directly influenced by the following phenomena: 1) time taken for cells to express the delivered nucleic acid molecules; 2) number of cells that incorporate the exogenous nucleic acid molecules; 3) intensity of the resulting expression; 4) cellular turnover rates; 5) vascular flow rates; 6) reliability of the process; 7) method driving nucleic acid molecule expression; and 8) possible injury that may result from the nucleic acid molecule delivery process.

Efficient gene transfer has been difficult to achieve routinely in the kidney, as illustrated by the varied levels of successful transgene incorporation reported in previous studies, and more generally, the failure of any of these methods to achieve widespread use. The structure of various renal vascular beds and their permeability characteristics present intrinsic challenges to gene transfer processes. For example, proximal tubule epithelial cells have an immense capacity for the apical endocytic uptake of exogenous materials, and thus the possibility of transgene incorporation. Yet, the accessibility of the apical domain to exogenously delivered vectors, and accordingly the resulting extent of transgene uptake, are strongly limited by the permeability characteristics of the glomerular filtration barrier. The degree to which proximal tubule cells are accessible for gene delivery at the basolateral surface, via the peritubular capillaries, is largely unknown.

In the kidney, previous studies have observed widely varying levels of gene expression using adenovirus vectors. In those studies, the adenoviral vectors were delivered through arterial injections in normal and cystic rats; via pelvic catheter infusion in normal rats; and via tail vein and cortical micropuncture injections in uninjured animals. For instance, adenovirus vectors delivered through intra-arterial injections to kidneys that were pre-chilled for extended periods generated transgene expression largely within the cortical vasculature; whereas the pre-chilling treatment, combined with vasodilators, facilitated gene transfer in both the inner and outer stripes of the outer medulla. However, expression in the cystic kidneys was only observed as patchy patterns in the vasculature, some epithelial cysts and interstitial cells.

Another group used adenovirus vectors to transduce rat glomerular endothelial cells by slow infusion into the renal artery. This technique resulted in transgene expression which lasted for at least 3 weeks without causing significant damage. However, expression was not observed within other cell types. Within the same study, analogous concentrations of the same adenovirus vector were delivered to the kidney via arterial injections and pelvic catheter infusions produced transgene expression in distinct, but still limited, regions of the kidney.

Comparably, studies using tail vein or retrograde ureteral adenovirus infusions, to target aquaporin water channels, also reported varied levels of expression that appeared to be dependent upon the transgene infusion site. Aquaporin 1 (AQP1) expression in apical and basolateral membranes of proximal tubule epithelial cells in the renal cortex, but no AQP1 expression was observed in glomeruli, loop of Henle, or collecting duct, when the virus was delivered by tail vein infusions.

Conversely, through ureteral infusions, significant ureteral and renal papilla transgene expression was reported, also with less intense and patchy expression observed in cortical collecting ducts.

Finally, others have explored direct transfer of adenovirus vectors into individual nephron segments using micropuncture techniques and achieved site-specific genetic incorporation within the injected tubules or vascular welling points. One limitation of the approach, however, is that gene expression is restricted to the injection site. There is also a risk of injury from transgene delivery via inflammatory responses generated from large concentrations of adenovirus vectors. Importantly, this result also demonstrated the utility of intravital fluorescent two-photon microscopy as a means of directly monitoring protein expression in live animals.

Lastly, acute kidney injury (AKI) remains a major clinical problem, as approximately 25% of ICU patients and 5-15% of all hospitalized patients experience this injury. Such patients observe increased risks of having their AKI progress to renal insufficiency, and ultimately dying during their hospitalization. Generally, AKI results primarily from direct renal trauma or blood loss, and the accumulation of various toxins, such as broad-spectrum antibiotics and chemotherapeutic agents, in proximal tubule epithelial cells. The management of AKI depends on the identification and treatment of its underlying cause, and current treatment regimes are mainly supportive. Intravenous fluid delivery is generally the first course of treatment for prirenal AKI, in the absence of hypervolemla. This standard approach is employed to prevent or eliminate volume depletions, remove tubular blockages, dilute toxin concentrations, facilitate diuresis and reinstate normal GFP levels. However, further studies are needed to determine exact fluid quantities and infusion endpoints for maximal interventional benefit.

AKI patients also have increased risk of progression to renal failure. AKI results from various etiologies including nephrotoxic agents, such as aminoglycosides, chemotherapeutic drugs and radiocontrast dyes. Management of AKI depends on identification and treatment of underlying causes, and current treatment regimens are mainly supportive. Gene therapy has been proposed as a novel alternative to treat, and possibly prevent AKI. While significant challenges to efficient renal gene transfer remain, the development of renal gene therapy by hydrodynamic gene delivery has shown promise in addressing this problem by providing substantial levels of reporter transgene expression in proximal tubule, which is the site of major damage during AKI.

SUMMARY OF THE INVENTION

The present invention provides, inter alia, an augmented hydrodynamic method for delivering fluid into a kidney cell of a mammalian subject, comprising: administering fluid into at least one kidney of a mammalian subject using the subject's renal vein as a guide for administering the fluid to the kidney, and wherein the fluid is administered to the kidney via the renal vein, under retrograde hydrodynamic pressure, and with temporary renal blood vessel occlusion.

Also provided are such methods, wherein the fluid further comprises at least one isolated nucleic acid molecule.

Also provided are such methods, wherein the isolated nucleic acid molecule is selected from the group consisting of: plasmid; naked plasmid; plasmid mixed with microspheres; nucleic acid in solution; virus particle; virus; combination of plasmid and virus particle; and artificial chromosome.

Also provided are such methods, wherein administration of the at least one nucleic acid molecule has a result selected from the group consisting of: nucleic acid molecule delivery to renal cortex and/or medulla; nucleic acid molecule delivery to glomerular, tubular, and/or vascular kidney cells; nucleic acid molecule expression in at least one kidney cell; increased degree of nucleic acid molecule expression in at least one kidney cell; sustained tissue morphology changes in at least one kidney cell; limited injury to kidney after administration of the at least one nucleic acid molecule; increased vector passage; increased vector efficiency; increased nucleic acid molecule and/or expressed protein diffusion; increased types of renal cells affected by nucleic acid molecule delivery; increased cavitation of renal cells; increased cell permeability; increased nucleic acid molecule delivery rate; increased stability of nucleic acid molecules administered; and diffuse cytosolic expression of nucleic acid molecules throughout cells.

Also provided are such methods, wherein the mammalian subject is selected from the group consisting of: laboratory animal; companion animal; draft animal; meat animal; and human.

Also provided are such methods, wherein the subject is a mammal selected from the group consisting of: cat; dog; horse; bovine; and human.

Also provided are such methods, wherein the mammalian subject has a kidney disease selected from the group consisting of: acute kidney failure; acute phosphate nephropathy; acute tubular necrosis; Alport syndrome; amyloidosis; analgesic nephropathy; antiphospholipid syndrome; apol1 mutations; Bartter syndrome; cholesterol emboli; contrast nephropathy; cryoglobuinemia; diabetes and diabetic kidney disease; diabetes insipidus; edema, swelling; Fabry's disease; fibrillary glomerulonephritis and immunotactoid glomerulopathy; focal segmental glomerulosclerosis, focal sclerosis, focal glomerulosclerosis; gestational hypertension; Gitelman syndrome; glomerular diseases; Goodpasture syndrome; hematuria (blood in urine); hemolytic uremic syndrome; high blood pressure and kidney disease; hyperaldosteronism; hypercalcemia (high blood calcium); hyponatremia (low blood sodium); hyperoxaluria; IgA nephropathy; IgG4 nephropathy; interstitial cystitis, painful bladder syndrome; interstitial nephritis; kidney stones; light chain deposition disease, monoclonal immunoglobulin deposition disease; Liddle syndrome; loin pain hematuria; lupus, systemic lupus erythematosis; lupus kidney disease, lupus nephritis; malignant hypertension; medullary cystic kidney disease; medullary sponge kidney; membranoproliferative glomerulonephritis; membranous nephropathy; metabolic acidosis; microscopic polyangiitis; minimal change disease; multiple myeloma; nail-patella syndrome; nephrocalcinosis; nephrotic syndrome; nutcracker syndrome; orthostatic hypotension; orthostatic proteinuria; post-infectious glomerulonephritis, post-streptococcal glomerulonephritis; polycystic kidney disease; preeclampsia; proteinuria (protein in urine); pyelonephritis (kidney infection); rapidly progressive glomerulonephritis; renal artery stenosis; renal infarction; renal tubular acidosis; reflux nephropathy; retroperitoneal fibrosis; rhabdomyolysis; sarcoidosis; scleroderma renal crisis; thin basement membrane disease, benign familial hematuria; tuberous sclerosis; tumor lysis syndrome; urinary tract infection; urinary tract obstruction; von Hippel-Lindau disease; warfarin-related nephropathy; and Wegener's granulomatosis.

Also provided are such methods, which further comprise a step prior to administering the fluid into the renal vein of a mammalian subject, the prior step selected from the group consisting of: administering an adjuvant; administering an anesthetic; administering an anticoagulant; administering a contractile agent; administering a relaxant agent; and administering a blood volume agent.

Also provided are such methods, which further comprises monitoring nucleic acid molecule delivery.

Also provided are such methods, wherein monitoring is accomplished by a method selected from the group consisting of: intravital multiphoton fluorescence microscopy and confocal laser scanning microscopy.

The present invention also provides methods for delivering at least one nucleic acid molecule to kidney cell of a mammalian subject, comprising: injecting a vector comprising at least one nucleic acid molecule into the mammalian kidney of a subject using the renal vein as a guide and under retrograde pressure.

Also provided are such methods, which further comprises clamping a blood vessel in the kidney so as to augment delivery of the nucleic acid molecule to the subject.

Also provided are such methods, wherein the vector is a viral vector.

Also provided are such methods, wherein the vector comprises human kidney regulatory elements.

Also provided are such methods, wherein the vector comprises a nucleic acid molecule useful to treat or prevent a kidney disease or condition.

Also provided are such methods to treat a kidney pathology in a subject having a kidney pathology, comprising: administering an appropriately therapeutic fluid according to a method herein to a subject having a kidney pathology and treating a kidney pathology in the subject.

Also provided are such methods to prevent a kidney pathology in a subject at risk of kidney pathology, comprising: administering an appropriately therapeutic fluid according to a method herein to a subject having a kidney pathology and preventing a kidney pathology in the subject.

Also provided are such methods to ameliorate at least one symptom related to a kidney pathology in a subject, comprising: administering an appropriately therapeutic fluid according to a method herein to a subject having a kidney pathology and ameliorating at least one symptom related to a kidney pathology in the subject.

Also provided are such methods to ameliorate at least one symptom related to acute kidney injury in a subject with a symptom related to acute kidney injury, comprising: administering an appropriately therapeutic fluid according to a method herein to a subject having acute kidney injury and ameliorating at least one symptom related to acute kidney injury in the subject.

Also provided are such methods, wherein the fluid comprises saline solution.

Also provided are such methods to prevent or ameliorate at least one symptom related to ischemia/reperfusion kidney injury in a subject at risk of, or having, a symptom related to ischemia/reperfusion kidney injury, comprising administering an appropriately therapeutic fluid according to a method herein to a subject at risk of, or having ischemia/reperfusion kidney injury and preventing or ameliorating at least one symptom related to ischemia/reperfusion kidney injury in the subject.

Also provided are such methods wherein the fluid comprises saline solution and/or at least one exogenous nucleic acid.

The present invention also provides methods to introduce at least one exogenous nucleic acid into at least one kidney cell of a subject in need thereof, comprising administering a fluid comprising at least one exogenous nucleic acid via retrograde hydrodynamic delivery of the fluid via the renal vein to at least one kidney cell of a patient in need of such administration, and wherein administration also includes temporary renal blood vessel occlusion, thereby introducing at least one exogenous nucleic acid into at least one kidney cell of a patient in need thereof.

Also provided are such methods wherein the length of time the fluid is administered is selected from the group consisting of: approximately 1 second to approximately 60 seconds; approximately 1 second to approximately 50 seconds; approximately 1 second to approximately 40 seconds; approximately 1 second to approximately 30 seconds; approximately 1 second to approximately 20 seconds; approximately 1 second to approximately 10 seconds; approximately 1 second to approximately five seconds; approximately five seconds.

Also provided are such methods wherein one or more exogenous nucleic acids are introduced at an efficiency selected from the group consisting of: approximately 10% or greater; approximately 20% or greater; approximately 30% or greater; approximately 40% or greater; approximately 50% or greater; approximately 60% or greater; approximately 70% or greater; approximately 80% or greater; approximately 90% or greater.

Also provided are such methods wherein one or more exogenous nucleic acids are introduced at an efficiency selected from the group consisting of: greater than 50%; 40% to 86%; and 78% to 86%.

Also provided are such methods wherein one or more exogenous nucleic acids are introduced into at least one superficial cortex cell at an efficiency selected from the group consisting of: approximately greater than 70%; approximately greater than 80%, and approximately greater than 90%.

Also provided are such methods wherein one or more exogenous nucleic acids are introduced at a depth of at least 100 µm and at an efficiency selected from the group consisting of: approximately 40% or greater; approximately 50% or greater; approximately 60% or greater; approximately 70% or greater; approximately 80% or greater; and approximately 90% or greater.

Also provided are such methods wherein at least some exogenous nucleic acids are retained in the at least one kidney cell for a time period selected from the group consisting of: greater than 2 days; greater than 3 days; greater than 4 days; greater than 5 days; greater than 6 days; greater than 7 days; greater than 14 days; greater than 21 days; and greater than 28 days.

Also provided are such methods wherein the exogenous nucleic acids are introduced to a depth of kidney cells selected from the group consisting of: at least about 100 µm; at least about 200 µm; at least about 300 µm; at least about 400 µm; at least about 500 µm, and greater than 500 µm.

Also provided are such methods, wherein the exogenous nucleic acids are introduced to kidney cells in a structure selected from the group consisting of: superficial cortex; cortex; cortico-medullary junction; medulla; nephron; glomerulus; and distal tubules.

Also provided are such methods, wherein the exogenous nucleic acids are introduced to kidney selected from the group consisting of: apical cells; basolateral cells; tubular epithelial cells; glomular cells; nephron cells; tubular interstitial cells; and tubular lumen cells.

Also provided are such methods, wherein efficiency is estimated by a measurement selected from the group consisting of: renal cell uptake; expression of at least one exogenous nucleic acid; at least one biomarker alteration; at least one chemical marker alteration; at least one cellular marker alteration; at least one structural marker alteration; at least one functional marker alteration; at least one cell viability marker alteration; at least one cell metabolism marker alteration; and at least one cell morphology marker alteration, wherein any alteration is measured compared to pre-administration of exogenous nucleic acid.

Also provided are such methods, wherein the at least one exogenous nucleic acid is a gene.

Also provided are such methods, wherein the at least one exogeneous nucleic acid is administered via an adenovirus.

Also provided are such methods, wherein the at least one exogenous nucleic acid is administered via a plasmid.

Also provided are such methods, wherein the nucleic acid is selected from the group consisting of: isocitrate hydrogenate 2; and sulphotransferase.

Also provided: gene therapy using any of the above compositions or methods; drug discovery using any of the above compositions or methods; kits using any of the above compositions or methods; assays using any of the above compositions or methods; compositions comprising any of the above compositions or methods; formulations comprising any of the above compositions or methods and using any of the above compositions or methods.

The terms "treat", "treatment," and "treating" and/or "ameliorating" include pathology reduction, reduction in symptoms, preventative (e.g., prophylactic) and palliative care.

In addition to the exemplary aspects and embodiments described above, further aspects and embodiments will become apparent by reference to the accompanying drawings forming a part of this specification wherein like reference characters designate corresponding parts in the several views.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1:
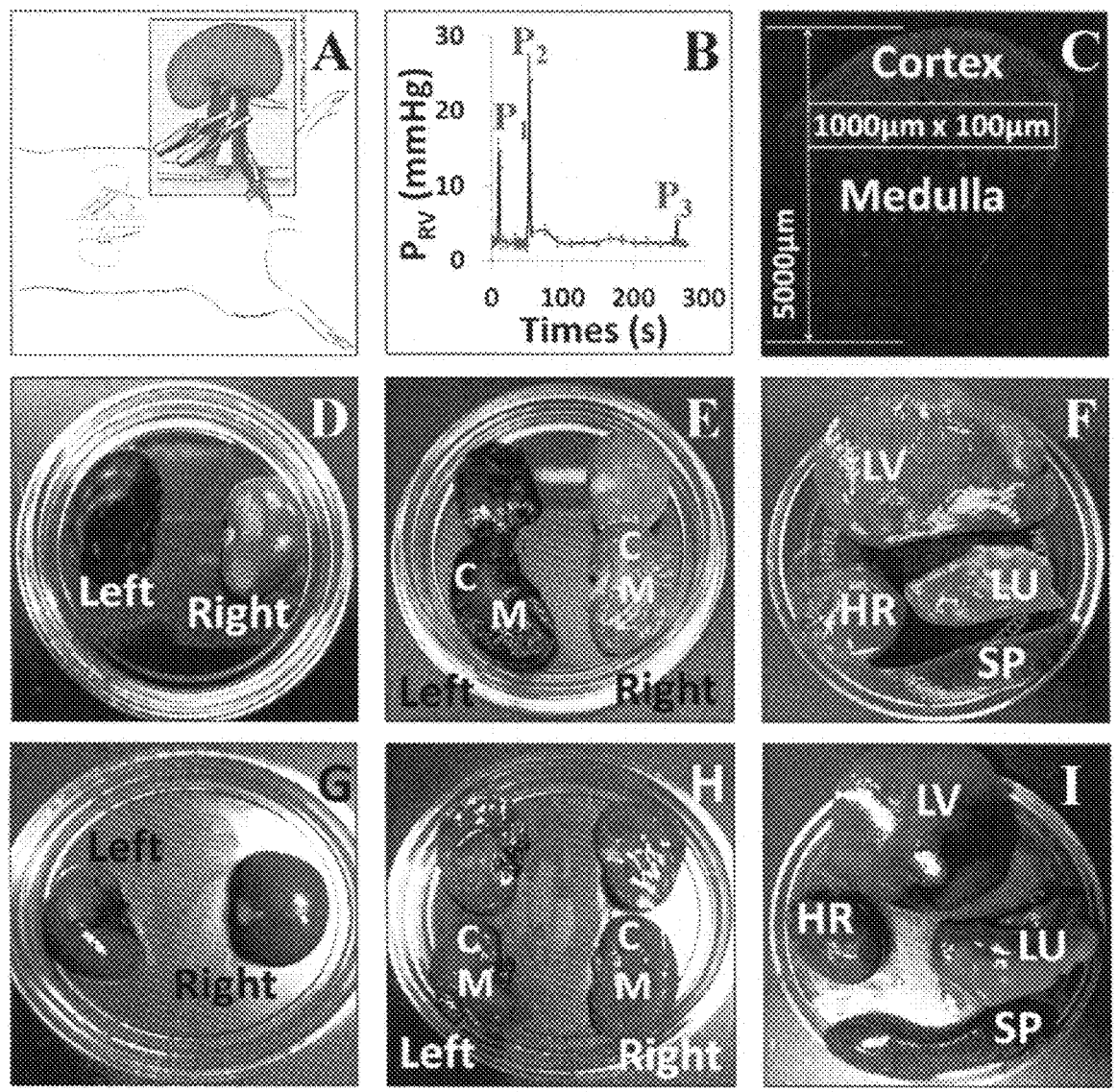
FIG. 1. (A) Schematic illustration of the hydrodynamic injection procedure. Following laparotomy to expose the left kidney, both the renal artery (red) and vein (blue) are clamped. Reagents to be delivered are injected into the renal vein at a site between the clamp and the kidney. (B) Pressure measured in the renal vein during the hydrodynamic delivery procedure. Pressures were measured using a damped ultrasonic Doppler flowmeter attached to a catheter inserted into the renal vein between the clamp and the kidney. P1: after both vascular clamps were applied; P2: hydrodynamic injection; P3: clamps removed. (C) Schematic illustration of the method used to analyze the efficiency of transfection in different regions of the kidney. The figure shows a montage of Texas Red-phalloidin labeled sections collected with a 60× objective and covering a wedge of the kidney extending from cortex to hylum. Efficiency of transfection was estimated in 100×1000 μm stripes located at various distances from the cortical surface as illustrated. (D)-(I) Organs (kidney; D, E, G, H), lung (LU), liver (LV), heart (HR) and spleen (SP) (F & I)) recovered from animals following hydrodynamic delivery of Toluidine Blue dye with (D-F) or without (G-I) clamping the renal artery and vein. The left kidney was injected in all cases.
Figure 2:
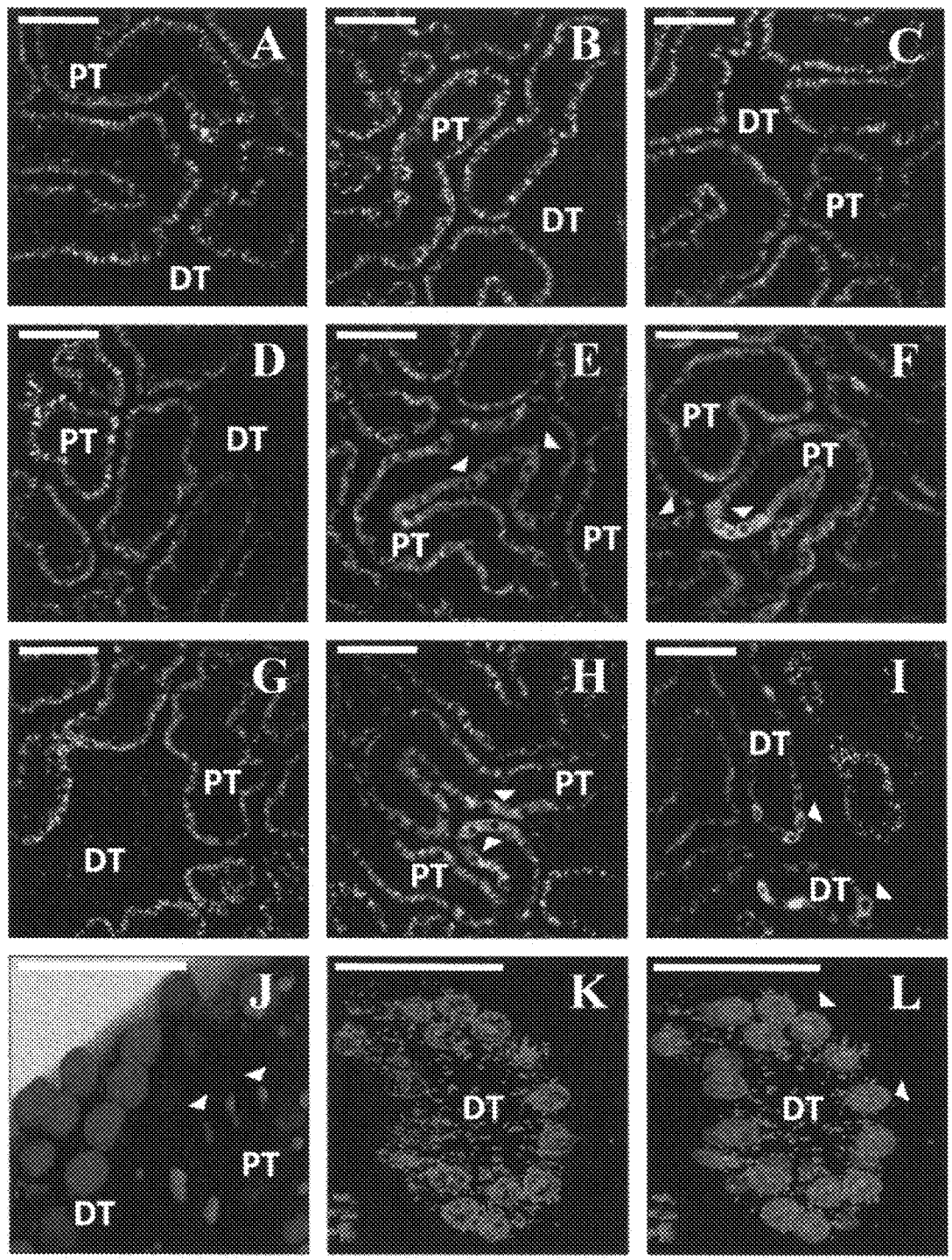
FIG. 2. Intravital imaging shows expression of fluorescent proteins from plasmid vectors. (A, D, G). Rat kidneys prior to hydrodynamic injection. Characteristic autofluorescence signal is detected in both the red and green channels. (B, C, E, F, H, I) Two representative fields collected from the same animals as in (A, D or G), using the same imaging parameters, 3 days after injection of saline (B,C), EGFP plasmid (E,F) or EGFP-tubulin plasmid (H,I). Arrowheads indicate tubular epithelial cells expressing the fluorescent proteins. (J). 3D rendering of a volume collected from an animal 3 days after injection of EGFP-occludin plasmid (green). Nuclei are labeled with Hoechst (blue). (K,L) A rat 1 day after injection of plasmid encoding tdTomato-histone H2B (red). Nuclei in (L) are labeled with Hoechst (blue). DT: distal tubule; PT: proximal tubule. Bars in all panels are 60 μm.
Figure 3:
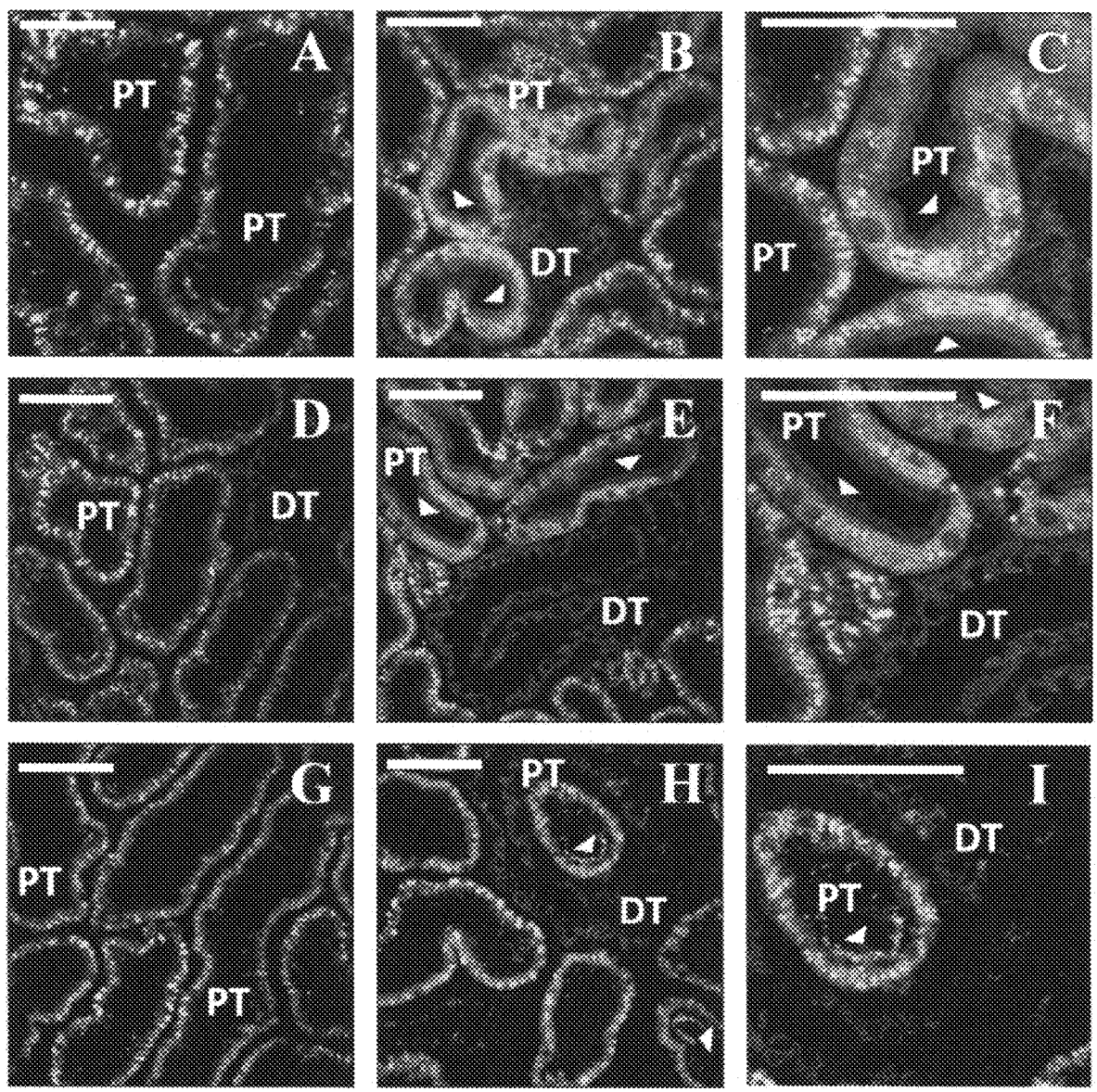
FIG. 3. Time course of expression of EGFP-actin from plasmid vectors. (A, D, G). Autofluorescence prior to injection. (B, C, E, F, H, I) Representative field, at two different magnifications, 3 (B,C), 14 (E, F) and 28 days (H, I) after hydrodynamic injection. Arrowheads indicate actin fluorescence in the brush border microvilli in proximal tubules. DT: distal tubule; PT: proximal tubule. Bars are 60 μm.
Figure 4:
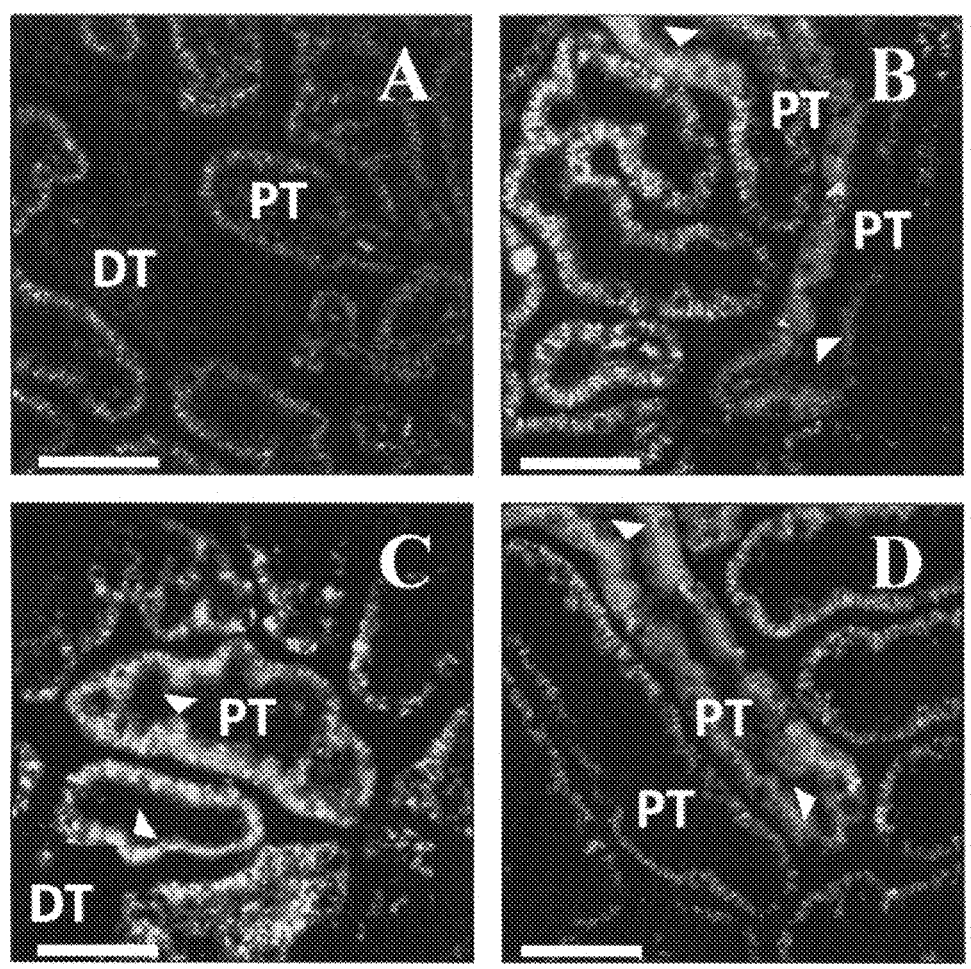
FIG. 4. Expression of EGFP-actin from adenoviral vectors. (A) Autofluorescence prior to injection. (B, C, D) Images collected 3 (B), 7 (C) or 14 (D) days after injection. Arrowheads show expression in proximal tubule epithelial cells. DT: distal tubule; PT: proximal tubule. Bars are 60 μm.
Figure 5:
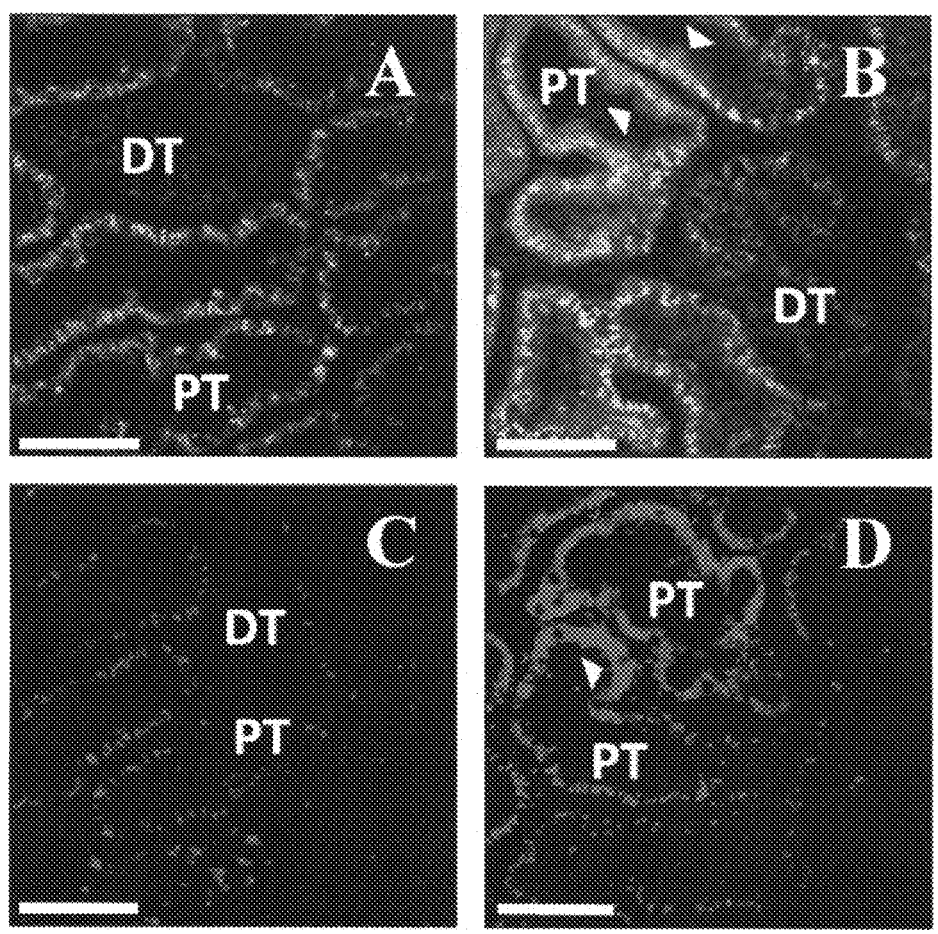
FIG. 5. Comparison of rats injected with EGFP-actin (B) or RFP-actin (D) adenovirus. Images were collected 3 days after injection. (A, C) Images collected prior to injection. DT: distal tubule; PT: proximal tubule. Bars are 60 μm.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION OF THE INVENTION

The inventors designed and characterized a method that utilizes renal vein-guided, retrograde pressurized injections to elicit transgene expression in mammalian kidneys. The inventors injected fluorescent albumin and dextrans into rodent renal veins under hydrodynamic pressure. These molecules were observed throughout renal segments using intravital fluorescence multiphoton microscopy. Thereafter, naked plasmids and baculovirus vectors, which express generalized and actin- and tubulin-targeting green fluorescent proteins, were introduced into live rodent kidneys in a similar fashion. Gene expression was then observed in live and ex vivo kidney segments using intravital microscopy, and confirmed in vitro with confocal laser scanning microscopy. The inventors recorded widespread transgene expression in live glomerular, tubular and vascular segments beyond a month after the introduction of the transgenes. Moreover, the naked plasmids provided two-fold increases in gene transfer efficiencies, with sustained tissue morphology.

The inventors have presented a method to rapidly deliver and monitor exogenous transgenes in live mammalian kidneys. In devising this technique, the inventors considered the following four criteria to achieve successful transformation: 1) a viable infusion site and vascular manipulations to produce widespread transgene delivery; 2) significant vector particle uptake by several renal cell types; and 3) limited general injury and vector derived toxicity.

In so doing, the inventors first determined which type of gene delivery method could potentially be used to overcome the innate structural barriers within the kidney, and supply a variety of renal compartments with exogenous genetic materials. Second, focus was then directed on identifying whether the hydrodynamic forces, generated from pressurized injections, would aid the passage of transgenes across epithelial and endothelial tissue structures, and ultimately their cellular incorporation. Third, it was then necessary to deduce which direct infusion port (renal artery, renal vein or ureter) would possess optimal characteristics (responses to contractile and relaxant agonists, and variations in compliance relative to increased blood volume) to withstand the effects of a pressurized injection.

Specifically, an optimal injection port would allow for a timely induction of hemostasis and minimize ischemia-reperfusion injury. This in turn would ideally permit the kidney to recover in a timely manner, providing no significant injury resulted from the injection process. Finally, it was necessary to investigate whether the choice of vector would generate appreciable levels of transgene expression in an efficacious manner.

The initial approach considered the renal artery as the infusion port. However, this method inhibited timely hemostasis after the injection and produced significant injury to kidney, low survival rates and rare signs of transduction. The inventors then switched to renal vein infusions. Using this injection site, the inventors considered a variety of vectors and tissue cavitation mechanisms for transgene expression. Naked DNA plasmids and plasmids mixed with microspheres, produced only limited success.

A second approach using augmented hydrodynamic delivery coupled with ultrasonic pulses, capable of disrupting lipid DNA complexes, resulted in limited improvements in transgene delivery. Nevertheless, the inventors found that hydrodynamic manipulation of the kidney, via the renal vein, resulted in the robust endocytic uptake of fluorescently tagged albumin and virtually eliminated surgery-related deaths. Based on these observations the inventors coupled hydrodynamic delivery with the use of baculovirus vectors. It was thought that the combination of a baculovirus vector in a relatively low titer would potentially facilitate endocytic virus incorporation and minimize resulting toxicity.

The GFP and Actin-GFP baculovirus vectors were then introduced into rodent kidneys using renal vein-guided, retrograde, pressurized injections. Transgene expression was then examined in these kidneys in live animals with intravital multiphoton fluorescence microscopy, and in tissue sections with confocal laser scanning microscopy. From these in vivo studies, transgene expression was detected within 24 hours of delivery, and the kidneys appeared to recover from the mild ischemic events (generated from the injection process) 3 days post transgene delivery. At that time point the inventors observed robust and lengthy glomerular, tubular and vascular transgene expression, generated from a single dose of low concentrations baculovirus injections.

Plasmid-derived transgene expression, generated from hydrodynamic injections coupled with vascular clamping, generated efficient, stable and widespread transfection with intact renal structure and function. The vast improvement in superficial cellular transformation will readily facilitate live renal studies. Moreover, the ability to utilize plasmid DNA for animal models offers the benefit of having a potent vector with a great safety profile and level of biocompatibility. Plasmids can also be used to readily generate large volumes of a wide palate of exogenous transgenes at relatively low costs to express.

These in vivo observations were confirmed by fixed tissue studies. In these studies robust signs of transgene expression were observed both superficially and within deep medullary compartments. Again, both non-specific, and actin-targeted and tubulin-targeted GFP expression was observed in cortex and medulla. Diffuse cytosolic expression was observed throughout cells infected with the GFP encoding vectors was observed. Likewise, increased GFP-based fluorescence originating from the cytoskeletal and apical brush border segments in cells infected with the actin-targeting vectors. The improved quality of the baculovirus-based protein expression can support the use of this technique for in vitro studies.

Overall, this simplified method provides an ability to rapidly and reliably deliver multiple types of exogenous genes to various nephron segments. Such a process increases widespread transgene expression. Without being bound by any particular theory, the observed transient increases in pressure may be sufficient to facilitate transgene uptake by basolateral anionic transporters and renal mechanotransduction, via the delivery of transgenes through stretch-gated ion channels. Alternatively, the non-specific affinity of plasmid DNA in a stand-alone form or bound to sera proteins, post its venous infusion, may benefit from enhanced endocytic uptake. This uptake may be triggered by rapid increases in fluid volumes, throughout the kidney.

Hydrodynamic transgene delivery also has side effects, which result in brief, mild, and reversible levels of tissue injury in live animals. This method allows one to modify renal segments at a measurable rate, while not inhibiting innate organ function. With the careful selection of reporter constructs this method provides a medium to simultaneously contrast and examine innate and abnormal cells/structures. Moreover, this method builds on the tradition of techniques like micropuncture transgene delivery, as it enables similar live delivery and monitoring, while providing widespread expression of biochemically relevant transgene concentrations.

Hydrodynamic-based cell transformation offers an attractive alternative to transgenic models, and may be used as a research tool for the study of normal and pathophysiological conditions in live mammalian systems. This method coupled with intravital multiphoton microscopy offers near real-time sub-cellular resolution. Thus, hydrodynamic cavitation has clinical utility in a strategy for genetic therapy.

The present invention provides methods to rapidly deliver exogenous genes, provide high-efficiency gene transfer and exceptional expression levels, along with monitoring methods related to their expression in live mammalian kidneys. Previous methods described in the literature have produced inconsistent or very limited expression, have required specialized equipment, were technically challenging to perform or required a tremendous commitment of time and resources in developing new animal strains. The methods are relatively easy for any reasonably skilled surgeon to perform, achieve consistent expression from procedure to procedure, provides relatively widespread and reasonably long-lived effects in the kidney, and provides minimal injury to the kidney. The inventors believe that the procedure described satisfies these criteria in that it provides for: 1) a viable infusion site and vascular manipulations to affect widespread transgene delivery; 2) a significant degree of vector uptake by several renal cell types; and 3) limited general injury and vector derived toxicity.

The innate structural barriers within the kidney pose significant obstacles to the delivery of exogenous genetic material to a variety of renal compartments. Delivery to the tubular epithelial cells, comprising a significant fraction of the renal parenchyma and a key target in many studies, has proved particularly challenging, due to the vascular microanatomy of the organ and the obstacle imposed by the glomerular filtration barrier on access to the tubule lumen. These considerations of tissue architecture probably account for the widely acknowledged failure of approaches such as systemic infusions of viral and plasmid vectors as useful methods for targeting most cells of interest in the kidney.

Straightforward surgical procedures allow easy access to the renal artery and vein and to the ureter and, in principle, any of the three vessels could provide a feasible access point for hydrodynamic delivery. However, the inventors found that injection into the renal artery proved unsuccessful due to the difficulty in achieving hemostasis without concomitantly inducing an appreciable ischemic injury to the organ. In contrast, using the renal vein as is described in the present invention proved to be surprisingly successful in achieving widespread expression of the fluorescent proteins used in the experiments.

The studies demonstrate that hydrodynamic forces produced by the injection into the vein allow macromolecules to breach barriers that normally circumscribe their passage through the kidney. High molecular weight dextrans could be easily observed in the tubule lumen, as could albumin. An explanation for this observation is that the glomerular filtration barrier is somehow breached by the hydrodynamic forces in the glomerulus that result from the injection. However, it is hard to conceive that these forces could be a simple increase in the pressure in the glomerular capillaries producing a failure in the barrier, since it is unlikely that delivery at the renal vein could produce an increase in pressure at the glomerulus outside the normal tolerance of the system. It is possible that other routes of access to the tubular epithelial cells are possible. These include access to the basal side of the cells via the peritubular capillaries, or possibly a breach of the tight junctions between the cells, which also provides an alternative mechanism to account for their observed appearance in the tubule lumen.

Whatever the mechanism, it is clearly transient, since only large macromolecules present in the vasculature at the time of the injection appeared to be able to access the tubule lumen or transfect the bulk of the cells in the kidney. It is reassuring for the potential utility of this technique that the physical effects of the injection are so short-lived. The effect also appeared to be entirely confined to the kidney whose renal artery was injected, since the contralateral kidney and other highly vascular organs appeared to be completely unaffected. The requirement for proximate delivery of the injection also accounts for the failure of systemic delivery methods to achieve the same results, even those using hydrodynamic delivery.

The method was particularly successful in achieving transfection of tubular epithelial cells. All segments of the nephron showed expression of the fluorescent proteins, with expression particularly prominent in the proximal and distal convoluted tubules. Other cell types also expressed the fluorescent proteins more sporadically, including cells in the glomerulus and the tubular interstitium. Cell-type specific expression of particular transgenes will require the use of specific promoters, and it is possible that a ureteral delivery method may be more optimal to efficiently target specific cell types.

The vectors used for delivery of the transgenes are a critical parameter in the success of efforts to express exogenous genes in the kidney. The high efficiency of viral infection has made these vectors a favorite of investigators in other fields, yet the inventors achieved essentially equal efficiency using plasmid vectors or adenovirus. Given the ease of preparation of plasmid vectors and the lesser degree of safety concerns surrounding their use compared to viral vectors, this is a very valuable aspect of this method.

Expression of the fluorescent proteins that were followed over a longer time course was remarkably persistent. There was only a moderate and progressive decline in the level of expression over a four-week period. Since the inventors did not use vectors designed specifically for integration into the host genome, incorporation of the sequences was presumably sporadic and infrequent. However, in the healthy adult kidney the rate of cellular turnover is thought to be relatively slow, and this may account for the fairly long-lived expression observed in the studies.

Baculoviral vectors produced the lowest efficiency of expression in the studies. The inventors have not investigated the reason for the discrepant behavior of these two systems, which may relate to compatibility with host cell surface molecules necessary for virus entry in the rat system. The baculoviral vectors also seemed to compromise the structure and function of cells that did become infected, as the inventors observed abnormal tubular morphology and fluorescent protein aggregates in cells that did exhibit expression. This contrasted with the observations with the plasmid and adenoviral vectors, where not only was tissue morphology normal in expressing regions but also the cells were clearly viable and metabolically active, as judged by their ability to actively internalize fluorescent dextrans from the tubule lumen.

It is desirable to provide methods in which long-term injury to the kidney is minimal Such injury could severely compromise the outcome of future studies. Ischemic injury to the kidney is a serious potential complication, since the procedure involves a brief period of hemostasis. Ischemic injury could clearly be observed in experiments where blood flow to the kidney was halted for more than 5 minutes, with the formation of debris or casts in the tubule lumen and sluggish microvascular flow in the peritubular capillaries. No such indications of injury were observed in the typical procedure, in which the vessels are clamped for only ~3 minutes or less. Good technique is thus clearly important, but the inventors believe this should be easy for a practiced surgeon to acquire. Investigators using this method should also carefully check for signs of injury using standard methods.

The inventors tried a number of more complex approaches. These included coupling hydrodynamic injections with ultrasonic pulsation, applied to enhance the disruption of lipid DNA complexes, or combining plasmid DNA with microspheres. None of these complex approaches augmented procedures enhanced the efficiency of expression compared to hydrodynamic delivery alone.

Widespread, stable and lengthy transformation recorded in various vascular, tubular and glomerular cell types accompanied intact renal structure and function. This vast improvement in superficial cellular transformation may be used to facilitate live renal studies that can be directed towards understanding and treating the underlying causes of renal disease.

The similar levels of expression obtained from both non-viral and viral vectors, which were limited to the kidneys that received hydrodynamic injection (no signs of expression were recorded in other organs post transgene delivery), outline the versatility of the gene delivery method for kidney-targeted gene transfer. Moreover, hydrodynamic delivery may also facilitate long-term investigations using helper-dependent or 3rd generation adenovirus systems that do not express capsid proteins and provide prolonged transgene expression.

However, in the case where the potential for mutagenesis derived over a long-term may be an issue, as has been reported with recombinant adenovirus systems, the ability to utilize plasmid DNA for animal models and human gene therapy offers the benefit of having a potent vector with a great safety profile and level of biocompatibility. Plasmids can also be used to readily generate large volumes of a wide palate of inexpensive exogenous transgenes.

Overall, this simplified method provides an ability to rapidly and reliably deliver multiple exogenous genes to various nephron segments with minimal injury. The uncharacteristic apical and basolateral incorporation, and filtration of large dextran molecules, as well as fluorescent protein expression observed in podocytes and epithelial cells of the S1 segment of proximal tubules may provide evidence that single hydrodynamic injections can facilitate their transient passage across the glomeruli filtration barrier.

Plasmid DNA (possible bound to sera proteins) and adenovirions may benefit from enhanced endocytic uptake (primarily in the tubules), triggered by rapid increases in renal fluid volume after their venous infusion. This technique provides large molecules the ability to access the lumens, and apical and basolateral borders of renal tubular epithelial cells.

It should also be noted that hydrodynamic transgene delivery also has side effects, which result in brief, mild, and reversible levels of tissue injury in live animals. This method allows one to modify renal segments at a measurable rate, while not inhibiting overall innate organ function. With the careful selection of reporter constructs this method can provide a medium to investigate real time subcellular events in vivo. Moreover, this method builds on the tradition of techniques like micropuncture transgene delivery, as it enables similar live delivery and monitoring, while providing widespread expression of biochemically relevant transgene concentrations.

In conclusion, hydrodynamic-based cell transformation offers an attractive alternative to transgenic models, and may also be used as a research tool for the study of normal and pathophysiological conditions in live mammals. This method coupled with intravital two-photon microscopy offers near real-time sub-cellular resolution. Thus, hydrodynamic retrograde pressurized fluid delivery may have future clinical utility as a strategy for human genetic therapy.

The present invention provides a simplified technique to rapidly induce and monitor transgene expression in live rat kidneys without significant injury. To achieve this aim the inventors utilized two-photon excitation and confocal laser scanning microscopy techniques to investigate hydrodynamic venous delivery of vectors, including plasmids, baculovirions, and adenovirions.

Using pressurized renal vein injections of plasmid DNA the inventors developed a method to produce robust exogenous protein expression in a renal injury model. Transgene expression was recorded in live rats with mild and moderate ischemia/reperfusion renal injury that received the hydrodynamic treatment 1 and 24 hours after injury. These results provide a novel platform to potentially facilitate the future study and management of AKI during the initial phase of injury and at the time of maximal damage.

Hydrodynamic fluid delivery addresses the problem of reduced kidney function in acute ischemia/reperfusion injury by providing substantial reductions in sera creatinine levels with a single retrograde infusion into the left renal vein of rats with acute ischemia/reperfusion injury. These results provide an exciting platform to potentially facilitate the future study and management of AKI prior to a disease state, and at the time of maximal injury (24 hours after the underlying insult occurs) in an attempt to limit or reverse such injuries.

Nucleic Acid Molecules

The nucleic acid molecule may encode, for example, a therapeutic protein or an RNAi cassette, such as a shRNA. Alternatively, the nucleic acid molecule may be used to repair or replace an endogenous gene, for example DNA used for homologous recombination, or an oligonucleotide used for gene repair. Modifications include, for example, modifying expression levels of the gene and/or replacing a mutant gene with a wild-type copy of the gene. The nucleic acid molecule may be DNA or RNA, including microRNA. Also preferably, the nucleic acid molecule is a DNA construct, in particular a cDNA or synthetic DNA, and can be further modified to improve transcription and/or translation in the host cell, or to reduce or minimize gene silencing. The nucleic acid molecule construct may comprise, operably linked, a promoter region, a nucleotide, and optionally, a termination signal. Preferably, this construct is part of a plasmid. Preferably, the cells or tissue are stably transfected so that the transplanted cells or tissue may act, for example, as a bio-factory to produce a therapeutic protein for a long period of time.

Multiple nucleic acid molecule sequences can be introduced into the cells or tissue, including multiple copies of the same nucleic acid molecule sequence and/or multiple copies of differing nucleic acid molecule sequences encoding for different therapeutic or marker proteins. In one embodiment, each nucleic acid molecule sequence is present on a separate polynucleotide construct, plasmid, or vector. In another embodiment, both nucleic acid molecule sequences are present on one polynucleotide construct, plasmid, or vector, with each sequence under the control of a separate promoter. Alternatively, and in yet another embodiment, both nucleic acid molecule sequences are present on one polynucleotide construct, plasmid, or vector, with the polynucleotide structured so that it is bicistronic and where both nucleic acid molecule sequences are under the control of a single promoter. These various embodiments are further described below.

With respect to the embodiments where two differing nucleic acid molecule sequences are present on one polynucleotide construct, plasmid, or vector, each sequence can be under the control of a separate promoter or can be under the control of a single promoter. In addition to a first nucleic acid molecule sequence encoding for a selected therapeutic protein, in this embodiment, a second nucleic acid molecule sequence encoding, for example, a second therapeutic protein or a marker is included in the construct. Expression of this gene may be constitutive; in the case of a selectable marker this may be useful for selecting successfully transfected cells or for selecting cells or transfected populations of cells that are producing particularly high levels or optimal therapeutic levels of the protein. It will also be appreciated that a selectable marker may be used to provide a means for enriching for transfected cells or positively selecting for those cells which have been transfected, before reintroducing the cells into the patient, as will be described below.

Markers may include selectable drug resistance genes, metabolic enzyme genes, fluorescent proteins, bioluminescent proteins, or any other markers known in the art. Exemplary fluorescent proteins include, but are not limited to: green fluorescent protein, cyan fluorescent protein, yellow fluorescent protein, DsRed fluorescent protein, AsRed fluorescent protein, HcRed fluorescent protein, and maxFP-green protein. When a marker gene is included in the vector construct, it will be appreciated that the marker can be used to quantify the amount of fluorescence after transfection and/or before transplantation and/or after transplantation. Quantitative determination of fluorescence can be undertaken after transfection but before transplanting the tissue using, for example, fluorescence microscopy, flow cytometry, or fluorescence-activated cell sorting (FACS) analysis, in order to quantify the expression of fluorescence markers ex vivo. After transplanting the tissue, in vivo monitoring of the extent of fluorescence, as a measure of production of the therapeutic protein, can be done by examining the patient with a fluorescent ophthalmoscope or a surgical microscope equipped for fluorescence imaging, and can be documented with a CCD camera. It will be appreciated that the marker gene can be used to indicate levels of transgene expression and can be monitored by a non-invasive or a minimally invasive procedure. If marker gene expression decreases, another tissue implant can be inserted into the patient to increase the level of therapeutic protein. By using a marker gene, diminished expression of the therapeutic protein can be recognized early, rather than waiting until decreased levels of the therapeutic gene lead to disease progression.

It will be evident that for many gene therapy applications, selection for expression of a marker gene may not be possible or necessary. Also, it is possible that for in vivo applications, vectors without any internal promoters may be preferable. Single transcription unit vectors, which may be bicistronic or poly-cistronic, coding for one or two or more therapeutic genes, may be designed.

Where two or more genes are present and under transcriptional control of a single promoter, there may be an internal ribosome entry site (IRES), e.g. from picornaviral RNA, to allow both genes to be separately translated from a single transcript. Retroviruses incorporating IRES sequences are known in the art, for example in U.S. Pat. No. 5,665,567. Briefly, in bicistronic or multicistronic vectors, the individual reading frames of the gene segments encoding the proteins lie on the transcription unit (expression unit). Expression of each cistron is effected using a single promoter, in conjunction with a specific nucleic acid molecule sequence, typically untranslated regions of individual picorna viruses, e.g. poliovirus or encephalomyocarditis virus, or a cellular protein, e.g. BiP. In the picorna viruses, a short segment of the 5' untranslated region, the so-called IRES (internal ribosomal entry site) functions as an initiator for translation of reading frames.

By way of a specific example, the cells or tissue can be transfected with a plasmid having one promoter that drives the expression of a first therapeutic protein, such as pigment epithelium-derived factor (PEDF), and of a selectable marker, such as a fluorescent protein like enhanced green fluorescent protein (eGFP) under control of a cytomegalovirus (CMV) promoter. The CMV promoter is positioned at the 5' end of the construct. Downstream of the 3' end of the CMV promoter is the PEDF nucleotide sequence that encodes for PEDF protein. In the 3' direction of PEDF is an IRES site, which is designed to allow translation of multiple genes on an mRNA transcript. Following the IRES site in the 3' direction is the eGFP coding sequence. The IRES will allow translation of eGFP as well as translation of PEDF.

The promoter region of the construct can be chosen from among all promoter regions that are functional in mammalian cells, in particular human cells. The promoter can be a strong or weak promoter, a constitutive or a regulated/inducible promoter, a ubiquitous or selective promoter. The promoter can be of different origin such as cellular, viral, artificial, and the like. Particular types of promoters are house-keeping promoters, i.e., promoters from cellular genes expressed in mammalian tissues or cells, or viral promoters (CMV, LTR, SV40, etc.). Furthermore, the promoter region can be modified artificially to include enhancer element(s), inducibility element(s) and the like. The promoter, secretion and termination region sequences can be selected and adapted by the skilled artisan based on the polypeptide, the pathology, the vector used, etc. In this regard, the nucleic acid molecule construct can be inserted into various kinds of vectors such as plasmids, episomes, artificial chromosomes and the like.

The nucleic acid molecule construct can optionally include a secretion signal, positioned between the promoter and coding regions, which allows, or facilitates, the secretion of the polypeptide outside of the cells. The secretion signal may be homologous with respect to the polypeptide (i.e., from the same gene) or heterologous thereto (i.e., from any other gene encoding a secreted polypeptide, in particular a mammalian gene, or artificial). Examples of secretion signals include the signal peptide of vascular endothelial growth factor (VEGF), pre pro nerve growth sequence (NGS), and the like.

Various approaches may be used to achieve long-term expression of the nucleic acid molecule in the cells or tissue. One approach involves a circular vector carrying a recombination site and the polynucleotide sequence encoding for the therapeutic protein, shRNA, miRNA, etc., and the transfection is accompanied by introduction of a recombinase that facilitates recombination between the vector's recombination site and a second recombination site in the genome of the cell being transfected. Constructs carrying a recombination site, such as a phiC31 attB site, have been described. It will be appreciated, however, that other means for long-term gene expression are contemplated, such as the other members of the serine recombinase family, transposases (e.g., "Sleeping Beauty"), DNA mini-circles, plasmids optimized for minimal gene silencing, or the use of a stable extrachromasomal vector such as EBV. When using a phiC31 attB recombination site, the nucleic acid molecule constructs are comprised of the phiC31 integrase system to achieve site-specific integration into a target genome of interest.

Bacteriophage phi-C31 integtrase recognizes pseudo-recombination sites present in eukaryotic cells. For genetic manipulation of a eukaryotic cell, phiC31 integrase and a vector carrying a phiC31 wild-type recombination site are placed into the cell. The wild-type recombination sequence aligns itself with a sequence in the eukaryotic cell genome and the phiC31 integrase facilitates a recombination that results in integration of a heterologous gene into the eukaryotic genome. It is contemplated that any attB site, any attP site, or any pseudo att site is present on any nucleotide sequence used to introduce genetic material into the genome of the harvested or cultured cells.

Accordingly, in one embodiment, the method of integrating a polynucleotide sequence into a genome of a cell comprises introducing into the cell (i) a circular targeting construct, comprising a first recombination site and a polynucleotide sequence of interest, and (ii) a phiC31 integrase, native or modified, wherein the genome of the cell comprises a second recombination site (ie. a pseudo att site) native to the human genome. Recombination between the first and second recombination sites is facilitated by the site-specific integrase.

The therapeutic gene and the attB sequence are preferably introduced into the target cell as circular plasmid DNA. The integrase may be introduced into the target cell (i) as DNA encoding the integrase on a second plasmid, (ii) mRNA encoding the integrase, or (iii) in polypeptide form. Once phiC31 is introduced into the cell, the cell is maintained under conditions that allow recombination between the first and second recombination sites and the recombination is mediated by the phiC31 integrase. The result of the recombination is site-specific integration of the polynucleotide sequence of interest in the genome of the cell.

Transfection of a wide variety of genes encoding for therapeutic proteins is contemplated, and preferred candidate genes include genes that encode for diffusible proteins that act extracellularly to have a therapeutic effect.

In some embodiments, the vector is a viral vector. "Viral vector" refers to recombinant viruses engineered to effect the introduction of exogenous nucleic acid molecules into cells. Viral vectors include, for example, retroviruses, adenoviruses, adeno-associated viruses (AAV), baculoviruses, vaccinia viruses, herpes viruses, alphavirsus vectors, alphavirus replicons and lentivirus vectors.

In specific embodiments, the viral vector may be a baculovirus vector. Baculovirus vectors, such as, for example, those derived from Autographa Californica Multicapsid Nucleopolyhedrovirus (AcMNPV) are useful in the present invention.

A person skilled in the art would readily appreciate how to construct baculoviral vectors for use in the invention. Recombinant baculovirus vectors may be constructed according to instructions accompanying commercial baculovirus expression systems, for example, the Bac-to-Bac™ Expression system (Invitrogen). Recombinant baculoviral vectors may be modified by molecular biological techniques, including PCR-based techniques and other cloning techniques, as will be known to a skilled person and described, for example, in Sambrook et al., Molecular Cloning A Laboratory Manual (3rd ed.), Cold Spring Harbour Press.

Viral vectors may be engineered to contain increased levels of the viral envelope glycoprotein gp64. Recombinant viral vectors may also be modified by incorporating foreign envelope proteins into the envelope of the viral virion. For example, increased neural infection efficiency may be achieved by pseudotyping rabies virus glycoprotein (RVG) or vesicular stomatitis virus G protein (VSVG), herpes envelope glycoprotein or envelope proteins derived from .alpha.- or rhabdovirus into the envelope of the viral virion. Alternatively, the cell specificity of viral infection may be increased by incorporating antibodies directed against cell-specific protein receptors into the viral envelope.

To minimize or avoid any possibility for inactivation by serum complement, recombinant viruses may be modified to increase their resistance to the complement system, including, for example, by incorporating human decay-accelerating factor into a viral envelope.

In other embodiments, the vector is a non-viral vector. "Non-viral vectors" refers to systems other than viral vectors that may be used to introduce exogenous nucleic acid molecules, for example plasmids, into a cell. Non-viral vectors include, but are not limited to polymer-based, peptide-based and lipid-based vectors. Many non-viral vectors are commercially available, such as, for instance PEI 25K (Sigma-Aldrich, St. Louis, Mo.) Lipofectamine™ 2000 (Invitrogen, Carlsbad Calif.). Complexes of these vectors and nucleic acid molecules may be prepared according to commercial instructions, or by following protocols known to a person skilled in the art, such as, for example, Boussif et al. (1995, Proc. Nat. Acad. Sci. 92:7297).

Generally, non-viral gene-delivery systems rely on the direct delivery of the target nucleic acid molecule or on nonspecific internalization methods. Non-viral gene delivery systems and methods for their transfection would be known to a person skilled in the art, and include, for example, naked plasmids, DEAE-dextran, calcium phosphate co-precipitation, microinjection, liposome-mediated transfection, cationic lipids, and polycationic polymers. As would further be appreciated by a person skilled in the art, some of these methods, such as, for example, microinjection, liposome-mediated transfection, polycationic polymers, are capable of transfecting cells both in vivo and in vitro. These non-viral vectors may be modified to enhance nerve-specific transfection, for example by linking the vector to one or more ligands that may specifically or preferentially bind to neuronal cells. For example, nerve-specific transfection of polylysine/DNA complexes may be obtained by covalently linking the nontoxic fragment C of tetanus toxin to polylysine.

Non-viral vectors containing DNA with bacterial sequences often have increased palindromic CpG sequences relative to eukaryotes, and these foreign CpG sequences may serve as strong immunostimulatory agents in vertebrates. Reducing CpG content therefore may be advantageous and may also enhance protein expression as CpG sequences may be methylated in eukaryotic hosts, which can result in the transcriptional silencing. In some embodiments, the CpG content of the DNA of non-viral DNA-based vectors is reduced. A person skilled in the art would readily appreciate that the CpG dinucleotide content of a vector may be reduced using standard molecular biology techniques, such as oligonucleotide or PCR-based mutagenesis as described, for example, in Chevalier-Mariette et al. 2003, Genome Biology 4:R53.

The transcriptional activity of a promoter in some instances may be weak, providing a less than ideal level of expression of therapeutic gene sequences. In various embodiments, the promoter may be operably linked to an enhancer. As would be understood by a skilled person, an "enhancer" is any nucleotide sequence capable of increasing the transcriptional activity of an operably linked promoter and, in the case of a neuron-specific promoter, of selectively increasing the transcriptional activity of the promoter in neuronal cells. A number of enhancers are known and a person skilled in the art would also know how to screen for novel enhancer sequences, for instance, by screening nucleotide sequences capable of increasing the transcription of a reporter gene, for instance, through functional mapping.

A first nucleic acid molecule sequence is operably linked with a second nucleic acid molecule sequence when the sequences are placed in a functional relationship. For example, a coding sequence is operably linked to a promoter if the promoter activates the transcription of the coding sequence. Similarly, a promoter and an enhancer are operably linked when the enhancer increases the transcription of operably linked sequences. Enhancers may function when separated from promoters and as such, an enhancer may be operably linked to a promoter even though it is not contiguous to the promoter. Generally, however, operably linked sequences are contiguous.

In different embodiments, the enhancer may be a heterologous enhancer, meaning a nucleotide sequence which is not naturally operably linked to a promoter and which, when so operably linked, increases the transcriptional activity of the promoter. Reference to increasing the transcriptional activity is meant to refer to any detectable increase in the level of transcription of an operably linked sequence compared to the level of the transcription observed with a promoter alone, as may be detected in standard transcriptional assays, including those using a reporter gene construct.

The enhancer may be a known strong viral enhancer element such as Rous sarcoma virus (RSV) promoter, SV40 promoter, CMV enhancer or promoter including CMV immediate early (IE) gene enhancer (CMVIE enhancer).

In different embodiments, the vector comprises a gene encoding a marker protein whose expression and cellular or subcellular localization may be readily determined "Marker protein" refers to a protein whose presence or subcellular localization may be readily determined, such as a green fluorescent protein (GFP) or any of its enhanced derivatives. Other marker proteins would be known to a person skilled in the art. In different embodiments, the gene may encode an enzyme whose expression may be readily determined by providing a specific substrate and detecting the products of enzymatic turnover, such as, for example, by providing luciferin to cell or cell lysates containing luciferase. In other embodiments, the marker protein may be any protein whose expression may be detected immunologically, for example by providing a labeled antibody that specifically recognizes the marker protein. The antibody is preferably a monoclonal antibody and may be directly or indirectly labeled according to methods known in the art, such as, for example, labeling with a fluorescent dye and detecting expression of the protein by fluorescence microscopy. Other immunological detection methods, including without limitation, immunogold staining, radiolabelling, colorimetric enzymatic precipitation would be known to a person skilled in the art.

Preferably, the vector comprises a therapeutic gene or a therapeutic transgene whose expression produces a therapeutic product. The term "gene" is used in accordance with its usual definition, to mean an operatively linked group of nucleic acid sequences. As used herein, "therapeutic product" describes any product that affects a desired result, for example, treatment, prevention or amelioration of a disease. The therapeutic product may be a therapeutic protein, a therapeutic peptide or a therapeutic RNA, such as, for example, a small interfering RNA (siRNA), microRNA or an anti-sense RNA.

To aid in administration, the vectors may be formulated as an ingredient in a pharmaceutical composition. The compositions may routinely contain pharmaceutically acceptable concentrations of salt, buffering agents, preservatives and various compatible carriers or diluents. For all forms of delivery, the vectors may be formulated in a physiological salt solution.

The proportion and identity of the pharmaceutically acceptable diluent is determined by chosen route of administration, compatibility with the vector and standard pharmaceutical practice. Generally, the pharmaceutical composition will be formulated with components that will not significantly impair the biological activities of the vector. Suitable vehicles and diluents are described, for example, in Remington's Pharmaceutical Sciences (Remington's Pharmaceutical Sciences, Mack Publishing Company, Easton, Pa., USA 1985).

Solutions of the vectors may be prepared in a physiologically suitable buffer. Under ordinary conditions of storage and use, these preparations contain a preservative to prevent the growth of microorganisms, but that will not inactivate the vector. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999.

In some embodiments, the vectors are administered to a vertebrate host. In a specific embodiment, the vectors are administered to a human host.

Effective amounts of vectors can be given repeatedly, depending upon the effect of the initial treatment regimen. Administrations are typically given periodically, while monitoring any response. It will be recognized by a skilled person that lower or higher dosages may be given, according to the administration schedules and routes selected.

When administered to a human patient, for example, the vectors are administered in an effective amount and for a sufficient time period to achieve a desired result. For example, the vectors may be administered in quantities and dosages necessary to deliver a therapeutic gene, the product of which functions to alleviate, improve, mitigate, ameliorate, stabilize, prevent the spread of, slow or delay the progression of or cure a peripheral neuronal neuropathy.

The effective amount to be administered to a patient can vary depending on many factors such as, among other things, the pharmacodynamic properties of the therapeutic gene product, the mode of administration, the age, health and weight of the subject, the nature and extent of the disorder or disease state, the frequency of the treatment and the type of concurrent treatment, if any. In embodiments employing viral vectors, the effective amount may also depend on the virulence and titer of the virus.

One of skill in the art can determine the appropriate amount based on the above factors. Vectors may be administered initially in a suitable amount that may be adjusted as required, depending on the clinical response of the patient. The effective amount of a vector can be determined empirically and depends on the maximal amount of the vector that can be safely administered. In some embodiments, the vector may have little cytotoxicity in vertebrates and may be administered in large amounts. However, the amount of vectors administered should be the minimal amount that produces the desired result.

In various embodiments, a dose of about $10^9$ recombinant baculovirus particles are administered to a human patient. In other embodiments, about $10^2$ to about $10^9$ recombinant baculovirus particles, about $10^6$ to about $10^9$ recombinant baculovirus particles, about $10^2$ to about $10^7$ recombinant baculovirus particles, about $10^3$ to about $10^6$ recombinant baculovirus particles, or about $10^4$ to about $10^5$ recombinant baculovirus particles may be administered in a single dose. In some embodiments, the vector may be administered more than once, for example, by repeated injections. In other embodiments, the viral vector may be repeatedly administered.

While a number of exemplary aspects and embodiments are discussed herein, those of skill in the art will recognize certain modifications, permutations, additions and sub-combinations therefore. It is therefore intended that the following appended claims hereinafter introduced are interpreted to include all such modifications, permutations, additions and sub-combinations are within their true spirit and scope. Each apparatus embodiment described herein has numerous equivalents.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and sub-ranges, as well as all individual values included in the ranges given are intended to be included in the disclosure. When a Markush group or other grouping is used herein, all individual members of the group and all combinations and sub-combinations possible of the group are intended to be individually included in the disclosure.

EXAMPLES

Example 1

Hydrodynamic Methods for Transgene Expression in Kidney Tissues

A. Materials and Methods

Cell Culture

Mouse Kidney Cell Culture.

The inventors used epithelial cells from the S3 segment of the proximal tubules. These cells were cultured in medium prepared by combining 500 ml of essential medium (Fisher Scientific, Pittsburgh, Pa.) with 7.5% of sodium bicarbonate, 7% of fetal bovine serum (FBS), and 1% of Pen-Strep, (Fisher Scientific, Pittsburgh, Pa.). The cells were grown in a 37° C., 5% $CO_2$, 38% $O_2$ humid incubator.

MDCK Cell Culture.

Madin-Darby Canine Kidney (MDCK) strain II cells, were grown in minimal essential media (Fisher Scientific, Pittsburgh, Pa.) with 8% fetal bovine serum, 1% L-glutamine, penicillin/streptomycin (Fisher Scientific, Pittsburgh, Pa.) and hygromycin (Calbiochem, San Diego, Calif.), and kept in a 37° C., 5% $CO_2$ humid incubator.

Rats

Male and female Sprague Dawley (Harlan Laboratories, Indianapolis, Ind.) and Munich Wistar rats (Fromter and Simonsen strains of Wistar rats were a gift of Dr. Bruce Molitoris, Indiana University School of Medicine), ranging in weight from 150 to 470 gm, were used for these studies. The rats were given free access to standard rat chow and water throughout the studies. All experiments were conducted in accordance with the National Institutes of Health Guidelines and were approved by the Indiana University School of Medicine Institutional Animal Care and Use Committee (IACUC).

Dyes and Fluorescent Probes

Tolonium Chloride. The inventors prepared stock solutions by dissolving 50 mg of tolonium chloride dye (Toluidine Blue O, Electron Microscopy Sciences, Fort Washington, Pa.), in 5 ml of 0.9% saline. 0.5 ml of this mixture was used for each hydrodynamic injection.

Albumin, Dextrans and Hoechst. The following fluorescent probes were used in the intravital two-photon fluorescent imaging studies: Texas Red labeled albumin in phosphate buffered saline (PBS) prepared by combing Texas red sunfonyl chloride from (Life Technologies, Carlsbad, Calif.) and albumin fraction V powder (Sigma-Aldrich, St. Louis, Mo.), 3 kDa Cascade Blue, 4 and 150 kDa Fluorescein Isothiocyanate (FITC) dextrans (Invitrogen, Carlsbad, Calif.); 150 kDa Tetramethyl Rhodamine Isothiocyanate (TRITC) dextran (TdB Consultancy, Uppsala, Sweden); and Hoechst 33342 (Invitrogen, Carlsbad, Calif.). The final albumin and dextran injection solutions were prepared from diluting 50 µl of each 20 mg/ml stock solution in 0.5-1 ml of saline, and 30-50 µl of Hoechst was diluted in 0.5 ml of saline.

Transgene Vectors

Plasmid Vectors. Plasmid DNA was isolated using Qiagen Maxi Prep systems (Qiagen, Chatsworth, Calif., USA). These plasmids encoded: enhanced green fluorescent protein (EGFP), EGFP-actin and EGFP-tubulin (Clontech Laboratories, Inc., Mountain View, Calif., USA); EGFP-occludin (a gift from Dr. Clark Wells, Indiana University School of Medicine); H2B-tdTomato (a gift from Dr. Richard Day, Indiana University School of Medicine). For hydrodynamic injections, the range of doses the inventors used was 1-3 µg of plasmid DNA per gram of body weight diluted in 0.5 ml of saline.

Baculovirus Vectors. Cellular Light™ GFP, EGFP-actin and Null (control) BacMam 2.0 baculovirus expression vectors were from Life Technologies (Carlsbad, Calif.). The EGFP-actin baculovirus vector encoded fluorescent proteins with a human sequence targeting them to both filamentous and globular actin. The Null reagent lacks mammalian genetic constituents, and is designed to identify potential baculovirus-mediated effects and distinguish fluorescence signals from innate tissue fluorescence. A range of doses was used, spanning $1\times10^5$ to $1\times10^7$ viral particles/ml, suspended in saline.

Adenovirus Vectors. Replication-incompetent EGFP-actin and RFP-actin adenovirus vectors (gift of Dr. James Bamburg, Colorado State University), were kept at concentrations of 3×108 pfu/ml in DMEM at −80° C. For injections, the inventors used $3\times10^5$ to $3\times10^7$ pfu of each adenovirus vector suspended in 0.5 ml of saline solution.

Retrograde Venous Hydrodynamic Injection

Rats were anesthetized by inhaled isoflurane (Webster Veterinary Supply, Inc., Devens, Mass.; 5% in oxygen), and then placed on a heating pad to maintain core body temperature of 37° C. Temperature was monitored using a rectal probe. The abdomen was shaved, cleaned with Betadine Surgical Scrub (Purdue Products L.P., Stanford, Conn.) and a midline incision was made to expose and isolate the left renal vein. The renal artery and vein were occluded with micro-serrefine clamps (Fine Science Tools (USA), Inc., Foster City, Calif.).

The vein was then elevated with either 3-0 or 4-0 silk suture thread (Fine Science Tools (USA), Inc., Foster City, Calif.). At that time 0.5 ml of fluorescent probe or transgene expression vector solution was infused retrograde into the vein (i.e. towards the kidney) over a period of approximately 5 seconds, using a 30-gauge stainless steel needle attached to a 1 ml syringe, at the site between the clamp and the kidney (FIG. 1A). The needle was removed, and pressure was applied to the injection site using a cotton swab, to induce hemostasis. The vascular clamps were removed (the venous clamp was removed before the arterial clamp) to restore renal blood flow. The total clamping period lasted not more than 3 minutes. After this, the midline incision was closed and the animal was allowed to fully recover.

Monitoring Vital Signs During Renal Vein Hydrodynamic Retrograde Infusions in Live Rats The inventors made incision in the legs of anesthetized rats to expose femoral arteries. The arteries were isolated with two 3-0 or 4-0 silk loops. Using mirco-serrefine clamps the inventors clamped off the artery and tied off the loops as well. Each loop was then clamped with a pair of hemostats to stiffen and elevate each artery. The inventors then made a small incision in the femoral artery and inserted a PE-50 tubing catheter into its lumen. The other silk loop was used to anchor the catheter in place. This tubing was attached to a three-way port that was linked to a PowerLab 8/30 data acquisition system (ADInstruments Colorado Springs, Colo.) to record temperature, blood pressure and heart rate.

Fluorescence Microscopy

Intravital and Ex Vivo Two-photon Fluorescence Microscopy. Each rat was given an intraperitoneal dose of 50 mg/kg pentobarbital and then placed on a heating pad to maintain a core body temperature of 37° C. Once the animal was fully sedated, its left side was shaved and a vertical flank incision was made to externalize the left kidney. The kidney was then positioned inside a glass bottom dish containing saline, which was set above either a 20× or 60× water immersion objective for imaging. Similarly, for ex vivo imaging, saggital plane sections of kidneys harvested from anesthetized rats were positioned inside the glass bottom dish containing saline.

Fluorescent images were acquired using an Olympus (City, State) FV 1000-MPE Microscope equipped with a Spectra Physics (City, State) MaiTai Deep See laser, with dispersion compensation for two-photon microscopy, tuned to 770-860 nm excitation wavelengths. The system was also equipped with two external detectors for two-photon imaging, and dichroic mirrors available for collecting blue, green and red emissions. The system was mounted on an Olympus IX81 inverted microscope. Bars in all figures are 60 µm.

Jugular Vein Infusions

Each rat was first anesthetized by inhaled isoflurane (Webster Veterinary Supply, Inc., Devens, Mass.), 5% in oxygen, and then given an intraperitoneal injection of approximately 50 mg/kg of pentobarbital. The rat was placed on a heating pad to maintain its core body temperature of 37° C. Once the animal was fully sedated, its neck was shaved and it was restrained on a heating pad. An incision was made to expose the jugular vein. The vein was isolated with two 3-0 or 4-0 silk loops. The loop closer to the animal's head was tied and clamped with a pair of hemostats to stiffen and elevate this vein. A small incision was then made in the jugular vein to insert a PE-50 tubing catheter into its lumen. The other silk loop was used to anchor the catheter in place. This tubing was attached to a 1 ml syringe containing the solution that would be infused into the vein.

Confocal Laser Scanning Fluorescence Microscopy

Whole kidneys were harvested from live animals directly before euthanasia. These kidneys were immersion fixed with 4% paraformaldehyde solution. After this, 100-200 µm thick sections were obtained using a vibratome. These sections were then mounted onto glass slides and imaged with the previously described Olympus IX81 inverted microscope in confocal mode.

Estimation of Transgene Delivery Efficiencies

The inventors used two-photon microscopy to analyze the time course and spatial distribution of renal transgene expression. The inventors estimated the transgene delivery efficiency for each vector in vivo using intravital fluorescent two-photon microscopy, and in vitro with confocal laser scanning microscopy. Using two-photon microscopy the inventors determined the efficiency of transgene expression within live superficial cortex segments of several rats across a 28-day period after transgene delivery. The inventors began the measurements 3 days after transgene delivery, having previously determined that this was the point when the inventors reproducibly observed signs of stable transformation and normal renal function.

For these efficiency measurements, the inventors set a threshold signal that was above the highest observed autofluorescence level and distinguished transgene expression from autofluorescent background. The inventors determined that transgene fluorescence signals had intensities at least double those of autofluorescence signals. Using these thresholds, the inventors then calculated the percentage of nephron cross-sections that expressed the reporter transgenes within fields acquired with the 60× objective. This final percentage (efficiency value) was calculated as the average percentage of transfected (transduced) nephron cross-sections within 10 randomly chosen adjacent fields.

Similarly, the in vitro estimations allowed the inventors to determine the degree of transgene distribution throughout all regions of the cortex and medulla, including those that are presently inaccessible by intravital two-photon microscopy. For these estimations the inventors first collected a montage of fields using confocal laser scanning microscopy covering a wedge of the kidney from the renal cortex to the level of the pedicle. Thereafter, the inventors estimated the extent of transformation using the same approach, within 100 µm×1000 µm regions.

Serum Creatinine Measurements

Creatinine levels were measured in serum samples obtained from rats used in these studies, using the creatinine kinase reagent set (Point Scientific, Inc., Canton, Mich.) in a Beckman Creatinine Analyzer 2 (Beckman Instruments, Brea, Calif.) Values are reported in mg/dl45.

Measurement of Hydrodynamic Injection Parameters

To characterize the hydrodynamic delivery process, the inventors monitored time-dependent pressure profiles during the injection with a damped ultrasonic Doppler flowmeter (Model T206, Transonic Systems, Ithaca, N.Y.). A PE-50 polyethylene catheter tubing (Clay Adams, Division of Becton, Dickson and Company, Parsippany, N.J.), was introduced into the femoral vein and traversed to the level of the bifurcation adjoining the renal vein and inferior vena cava.

B. Widespread Fluorescent Protein Expression Observed in Various Renal Segments In Vivo, Ex Vivo and In Vitro The inventors detected widespread and reproducible expression of a variety of fluorescent protein constructs delivered using the hydrodynamic method. The inventors observed a typical autofluorescent signature and normal morphology in kidneys that were not injected or injected with saline alone (FIGS. 2-8). Following hydrodynamic delivery of plasmid/adenovirus vectors, the inventors observed abundant expression of fluorescent proteins by in live kidneys (FIGS. 2-8). The fluorescent protein signals (FIGS. 2-8) were at least double the intensity of the autofluorescence (FIGS. 2-8) and showed characteristic spectral distributions that clearly distinguished them from the endogenous autofluorescence. Widespread transgene expression was observed as early as 24 hours after hydrodynamic delivery. During the first 36 hours after transgene delivery the inventors did occasionally observe cellular debris within tubule lumens. Such tissue damage may have resulted from the hydrodynamic forces produced by the injection or from mild ischemia-reperfusion injury associated with the injection process. However, this minimal injury completely subsided after this period, and at 3 days after the injection the kidneys appeared to be stable without signs of injury. The inventors carried out further studies to confirm that the kidney had not sustained significant injury (see below).

Figure 6:
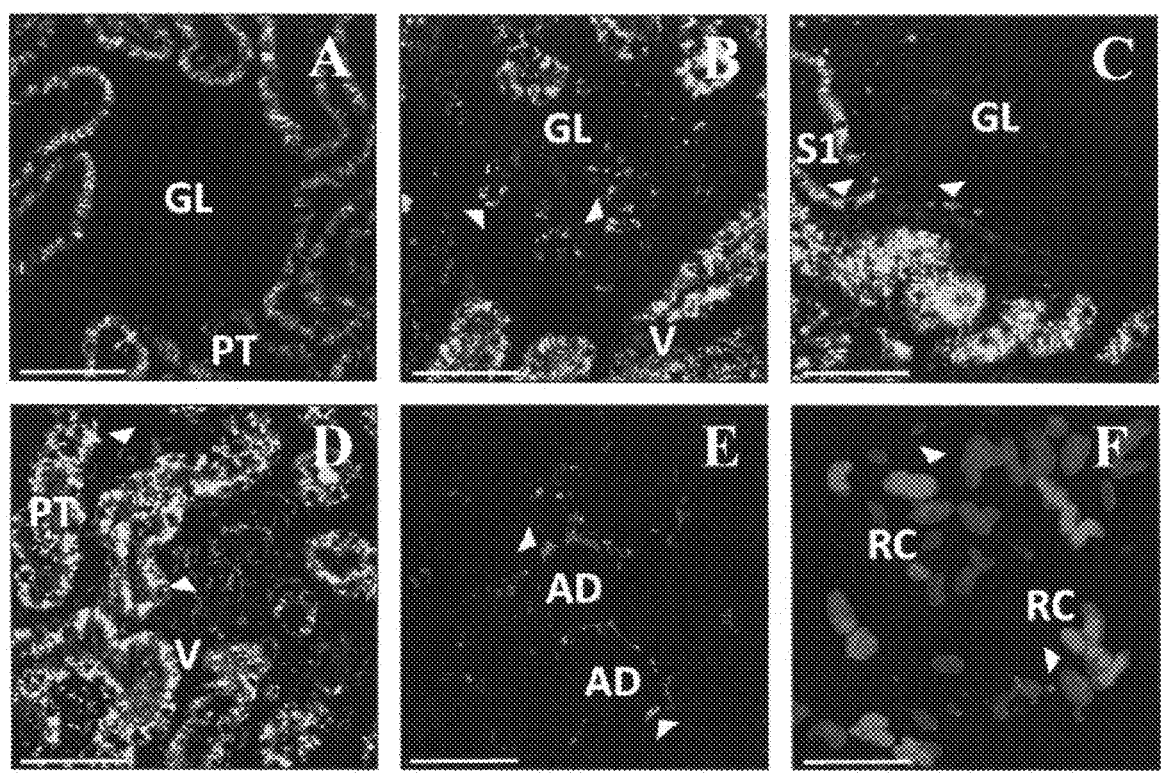
FIG. 6. Expression of EGFP-actin (B, C, D, E) from plasmid vectors in other kidney cell types (see text). (A) Autofluorescence observed 3 days following saline injection. Expression of EGFP-actin 3 (B, D, E) or 5 (C) days after injection. (F) Expression of td-Tomato-H2B (red) one day after injection. Nuclei are labeled with Hoechst (blue). GL: glomerulus; PT: proximal tubule; V: microvasculature; S1: S1 segment of proximal tubule; AD: adipocyte in perirenal fat; RC: renal capsular cells. Bars are 60 μm.
Figure 7:
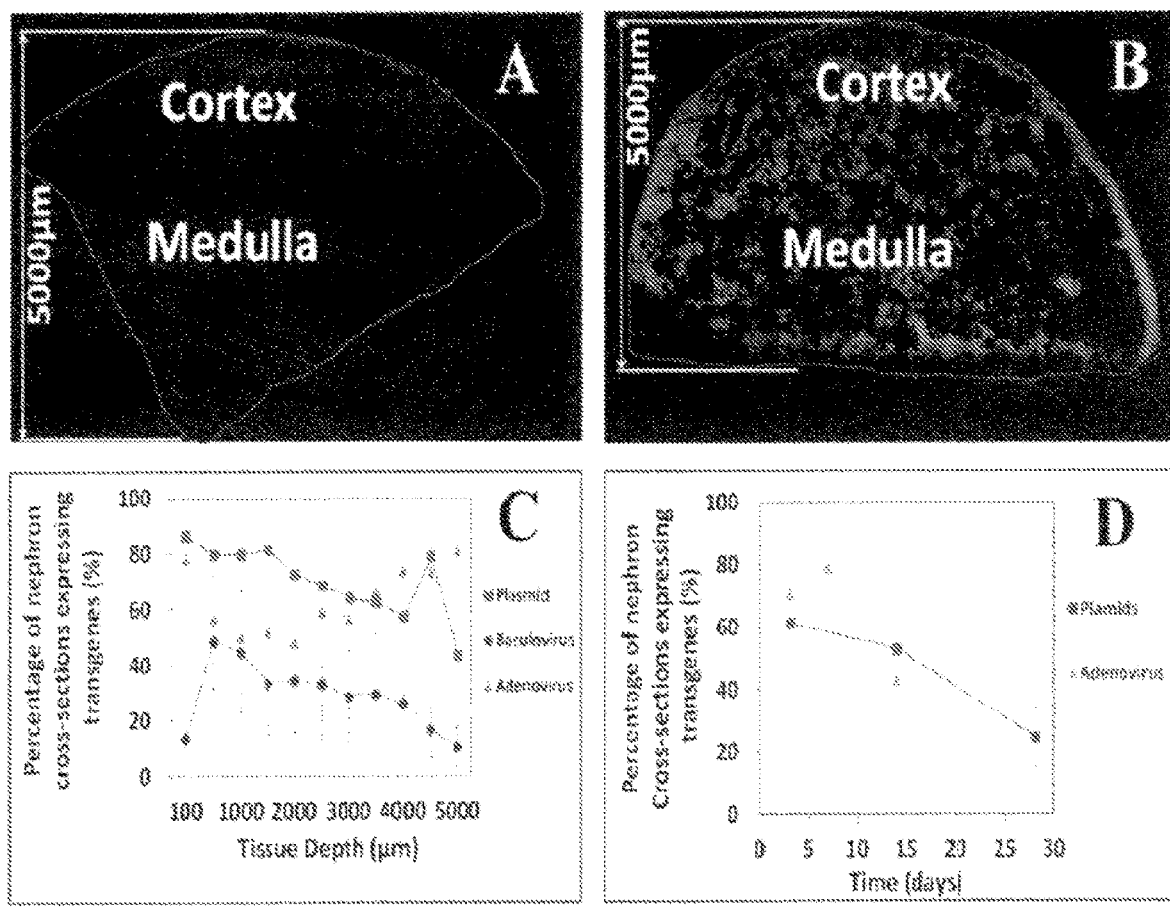
FIG. 7. Quantitative analysis of fluorescent protein expression following hydrodynamic delivery. (A, B) montages collected from fixed kidneys 3 days following injection of saline (A) or EGFP-tubulin (B). (C) Expression of EGFP-tubulin from plasmid vectors; expression of EGFP-actin from baculovirus or adenoviral vectors at the indicated distances from the cortical surface of the kidney 3 days after injection. (D) Expression of EGFP-actin from plasmid or adenoviral vectors estimated from intravital fields at the indicated times following injection.

Expression of a variety of fluorescent proteins was observed within live proximal and distal tubules (FIGS. 2-8); glomeruli (FIGS. 6B and 6C); the supporting interstitium (FIG. 6D); in adipose tissues at the surface of the kidney (FIG. 6E); and the renal capsule (FIG. 6F). Fluorescent protein expression was not limited to the superficial cortex, but it was necessary to use confocal microscopy of fixed tissues from injected animals to document expression in these deeper regions, which are presently inaccessible to two-photon intravital imaging. High levels of expression were found to extend across the cortex and medulla to the level of the papilla (FIG. 7B). Furthermore, it should be noted that single hydrodynamic injections of a mixture of EGFP-actin and RFP-actin adenovirus vectors generated the simultaneous expression of both fluorescent proteins, sometimes in the same cell, indicating that this method can be used for simultaneous expression of multiple genes.

The morphology of nephron segments expressing fluorescent proteins from plasmid vectors appeared normal.

Likewise, injections of adenovirus vectors ($3 \times 10^5$ pfu) resulted in stable transgene expression with normal tissue morphology. However, injections of higher titers of adenovirus ($3 \times 10^6$-$3 \times 10^7$ pfu) resulted in fluorescent debris/casts (within tubular lumens) that persisted beyond 3 days after viral delivery, indicating a possible immunological response to higher viral titers. In comparison, following the delivery of baculovirus vectors, areas that expressed fluorescent proteins generally deviated from normal tissue morphology and showed fluorescent protein aggregation.

Images obtained from rats that received hydrodynamic injections of plasmids that expressed EGFP-occludin and H2B-tdTomato fluorescent proteins provided clear signs of proper probe localization and morphology. For instance, EGFP-occludin signals ran between adjacent nuclei as punctate fluorescent bands along regions that would correspond to tight junctions (FIG. 2J). Fluorescent histone protein signals from H2B-tdTomato protein expression co-localized with nuclei counterstained with Hoechst (FIG. 2L).

Similarly, in images taken from rats injected with plasmids (FIG. 3), or adenovirus vectors containing EGFP-actin (FIGS. 4 and 5) and RFP-actin (FIG. 5), there was characteristic labeling of the brush border in proximal tubules that expressed these transgenes.

Transgene expression in the glomerulus was investigated primarily in Wistar rats (FIGS. 6B and 6C). These rats have superficial glomeruli that are routinely accessible for imaging by two-photon microscopy. The inventors also visualized glomerular transgene expression in a Sprague Dawley rat on the rare occasion that this structure appeared within the range of two-photon imaging in this rat strain. Glomerular morphology was grossly normal in rats that received hydrodynamic saline injections (FIG. 6A).

The appearance of fluorescent protein distribution was consistent with expression in podocytes (FIG. 5B) Similarly, fluorescent protein expression was visualized in S1 segments of proximal tubules and parietal epithelial cells of the Bowman's capsule (FIG. 5C). Additionally, 150 kDa TRITC dextran molecules, introduced into the jugular vein of animals that had previously been subject to hydrodynamic plasmid delivery, were characteristically confined to the vasculature (FIGS. 5B and 5C). This provided further evidence of maintained glomerular structural and functional integrity following transgene delivery and expression.

Plasmid- and adenovirus-derived fluorescent protein expression was also present in cells within the peritubular interstitium that had morphology similar to either endothelial cells or monocytes (FIG. 5D), as well as in cells adjacent to the renal capsule (FIG. 5F). Strikingly, no signs of fluorescent protein expression were found in the contralateral kidney (i.e. non-injected kidney) or the other highly vascular organs examined (heart, liver, lung and spleen).

Hydrodynamic Injections can Generate Efficient Levels of Transgene Expression in Mammalian Kidneys The inventors examined tissue sections harvested from rats 3 days after they were treated with plasmids, baculovirus and adenovirus vectors, to gain insight into the efficiency of the hydrodynamic delivery method for each type of vector. For this work the inventors used confocal laser scanning microscopy to visualize fluorescent protein expression in kidney sections encompassing the entire depth of the kidney, from the cortical surface to the level of the renal pedicle (FIG. 7B). With plasmid or adenovirus vectors the inventors typically saw that multiple cells (greater than 50%) in a particular tubular cross-section simultaneously expressed the fluorescent proteins. However, using baculovirus vectors the inventors frequently observed only single cells expressing the fluorescent proteins.

Baculovirus-based transformation provided the lowest delivery efficiencies ranging from 10 to 50% of nephron cross-sections (FIG. 7C). In particular, within the most superficial cortical regions, which would be accessible by intravital two-photon microscopy, there was a 10% efficiency. However, at depths greater than 500 µm there was a gradual decrease in fluorescent protein expression in regions that would correspond to the deeper cortex, cortico-medullary junction and medulla.

Much higher levels of fluorescent protein expression were obtained using plasmid and adenovirus vectors (FIG. 7C). Using these vectors, 40 to 86% of nephron segments showed fluorescent protein expression. Within the superficial cortex (less than 100 µm from the surface), the inventors saw approximately 78-86% of nephron cross-sections expressing fluorescent proteins, explaining the relative ease with which expression was detected in live animals.

The high level of fluorescent protein expression in this superficial region of the cortex permitted the inventors to investigate the level of expression as a function of time by imaging live animals over a 4-week period. Over this period, the percentages of nephron cross-sections expressing fluorescent proteins ranged from 80 to 14% using adenovirus vectors, and 61 to 28% with plasmid vectors (FIG. 7D). Thus, expression appears to be relatively long-lived with even the rudimentary vectors used in this study.

C. Nephron Structure and Function Appear Normal after Hydrodynamic Delivery

The inventors looked for evidence of injury following hydrodynamic gene delivery by examining kidney structure and function using several approaches. In animals injected with high molecular weight dextrans (150 kDa TRITC) via the jugular vein, the inventors observed robust perfusion of the peritubular vasculature and confinement of the dextran by the glomerular filtration barrier. The inventors extended this analysis by simultaneously injecting high (150 kDa) and low (3 kDa) dextrans labeled with TRITC and Cascade blue respectively via the jugular vein. This analysis was conducted on rats from 3 to 28 days after they received hydrodynamic transgene injections of plasmids and adenovirus vectors. In all cases, after infusing the dextrans, the inventors observed the rapid appearance of both dextrans in the kidney by intravital two-photon microscopy. Large molecular weight dextran molecules were restricted to the vasculature, while low molecular weight dextran molecules passed the glomerular filtration barrier, where they gained access to the lumens of proximal tubules, and were rapidly endocytosed by proximal tubule epithelial cells, and were then concentrated within the distal tubule lumens (FIG. 8D). Importantly, dextrans were taken up equally well by cells expressing fluorescent proteins, indicating that these cells were viable and metabolically active. These data were confirmed by histology studies (FIGS. 8G and 8H), that showed normal renal structure within this timeframe. However, baculovirus vectors appeared to alter renal structure beyond the 3 day period.

D. Serum Creatinine Levels and Vital Signs are Unaffected by the Hydrodynamic Transgene Delivery Process The inventors monitored creatinine levels in normal rats that received hydrodynamic injections of saline alone or vectors. Creatinine levels in these rats remained within normal baseline levels (0.3 to 0.5 mg/dl) throughout the measurement period of up to 14 days after receiving hydrodynamic fluid delivery. There was no significant difference in the levels in rats that received isotonic fluid and those that received vectors. Similarly, blood pressure, body temperature and heart rate were all unaffected by the injection process.

E. Pressurized Retrograde Venous Injections Provide Widespread Delivery of Exogenous Macromolecules to the Kidney, and Restricts its Distribution to the Target Kidney The inventors attempted to clarify the mechanism that permitted highly efficient introduction of exogenous genes into the cells of the kidney. The inventors first investigated the extent of renal uptake that could be attained with solutions injected using this method. For these studies, live rats received hydrodynamic injections of 0.5 ml of toluidine dye solutions. The inventors then harvested whole left and right kidneys, hearts, livers, lungs and spleens from these rats. Saggital plane sections of these organs revealed robust distribution of the toluidine dye within the left (injected) kidney, and no traces within the contralateral kidney and the other organs examined when the injection process was performed as described above.

In comparison, hydrodynamic injections that were conducted without clamping the renal artery and vein (an approach used unsuccessfully in the early attempts to achieve expression of fluorescent proteins) resulted in minimal uptake of the dye within the target organ (left kidney), and significant levels within the aforementioned offsite and highly vascular organs.

F. Hydrodynamic Delivery Facilitates the Robust Cellular Internalization of Low, Intermediate and High Molecular Weight Exogenous Macromolecules Throughout Live Kidneys The inventors next investigated whether hydrodynamic infusions could reliably facilitate the cellular uptake of large macromolecules in various nephron segments in live animals. For this study, saline solutions containing either both low (3 kDa Cascade Blue), and intermediate (Texas Red labeled albumin) or large (150 kDa TRITC) or only low molecular weight dextrans were injected into the left renal veins of live rats.

Figure 8:
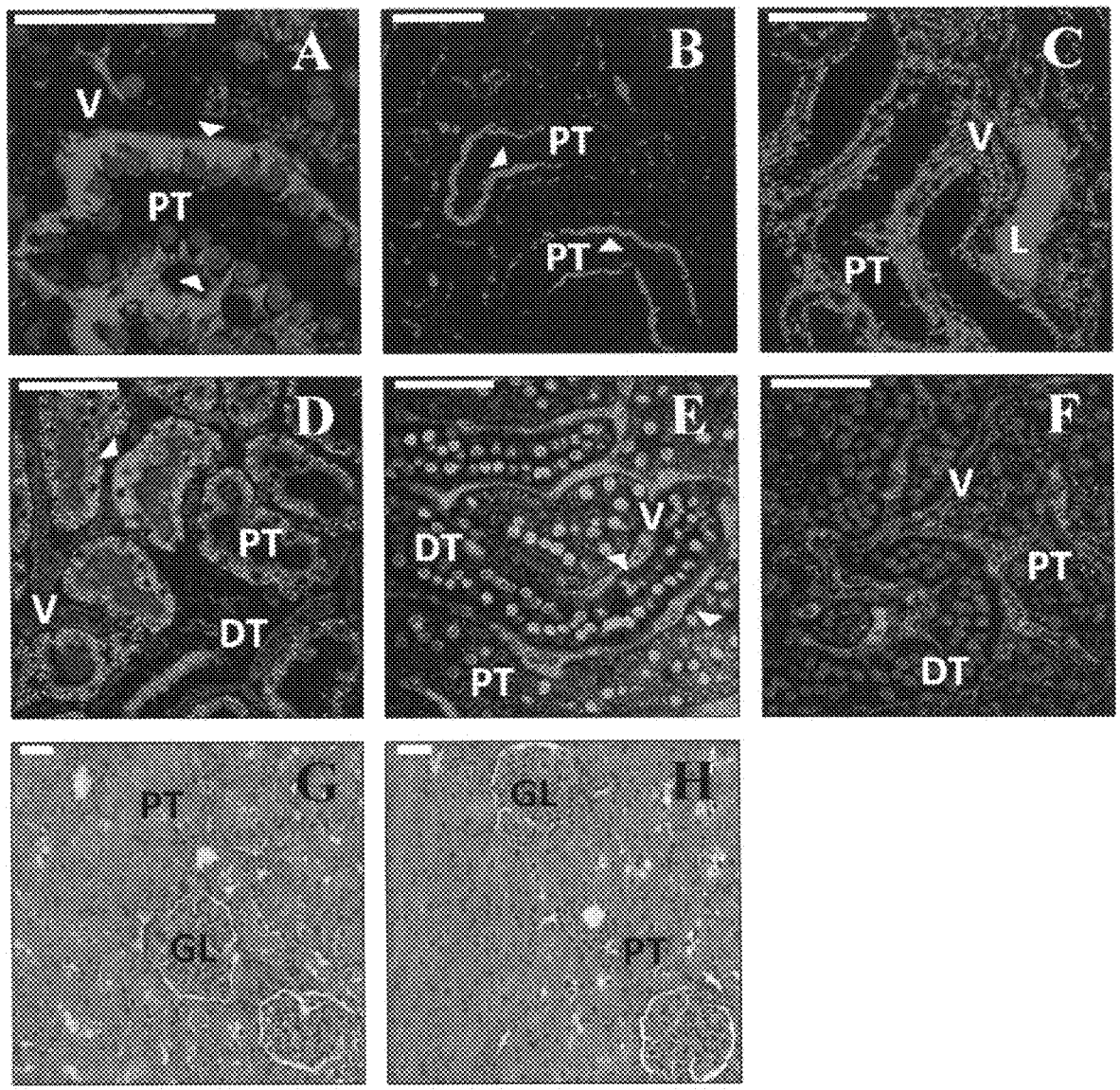
FIG. 8. Assessment of kidney structure and function following hydrodynamic injection and expression of fluorescent proteins. (A, B, C) Intravital imaging of rat kidneys ~20-30 minutes following hydrodynamic injection of a 150 kDa TRITC dextran (red). The dextran is rapidly internalized by proximal tubule epithelial cells (A), is visible at the basolateral surface (arrowhead in (A)) and frequently detected at the apical surface of these cells (arrowheads in B). In some instances, bright fluorescence was detected in the lumen of the tubule (C). (D) Rat kidney 3 days following injection of EGFP-actin plasmid (green). The kidney was injected with 3 kDa Cascade Blue dextran and 150 kDa TRITC dextran via the jugular vein ~20 minutes prior to imaging. Arrowhead shows abundant endocytosis of dextran in cells that express high levels of the fluorescent protein. (E) Rats were injected with 150 kDa FITC dextran via the jugular vein 5 minutes prior to hydrodynamic injection of saline into the renal vein. FITC dextran is confined to the vasculature (arrowhead) and is not detected at significant levels in the tubule lumen. (F) Injection of 150 kDa FITC dextran 20 minutes following hydrodynamic injection of saline. FITC fluorescence remains confined to the vasculature. (G, H) H&E stained sections from kidneys 3 days after saline (G) or EGFP-actin (H) injection. PT: proximal tubule; V: microvasculature; L: tubule lumen; GL: glomerulus.
Figure 9:
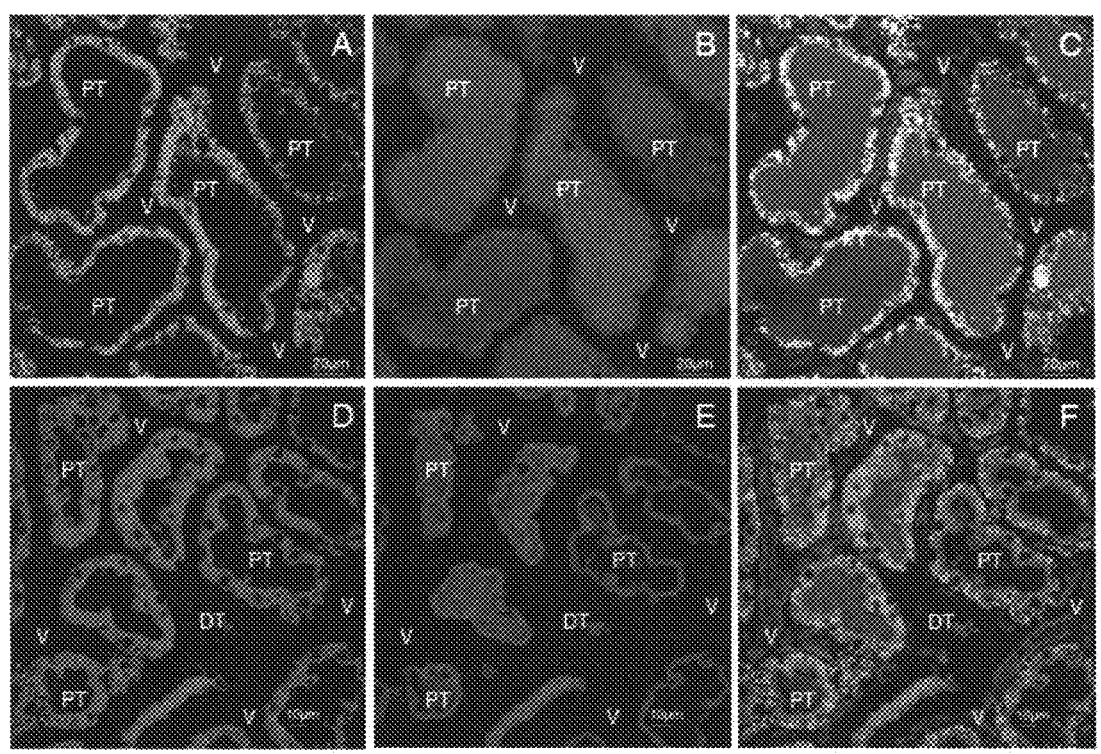
FIG. 9A-FIG. 9F. These data provide signs of intact renal structural and function capacities post hydrodynamic transgene delivery. The data are taken from a live rat 3 days after it was treated with pEGFP and PEGFP-Actin naked plasmin vectors. Images (A-C) outline pEGFP and (D-F) outline pEGFP-Actin transgene expression in proximal tubule (PT) epithelial cells. Solutions containing 3 kDa Casacde blue and 150 kDa TRITC dextrans were infused into the jugular veins of live rats. Robust and widespread uptake of the low molecular weight dextran solutions was observed after dye infusion, presented in images (B) and (E). The Cascade blue dextran was rapidly filtered by glomeruli, and was then endocytosed by into proximal tubule epithelial cells. Additionally, the large molecular weight dextran was restricted to the vasculature as shown in images (C) and (F), as observed in FIGS. 2A and 2B. Images (C and F) are the merger of blue, green and red channels.
Figure 10:
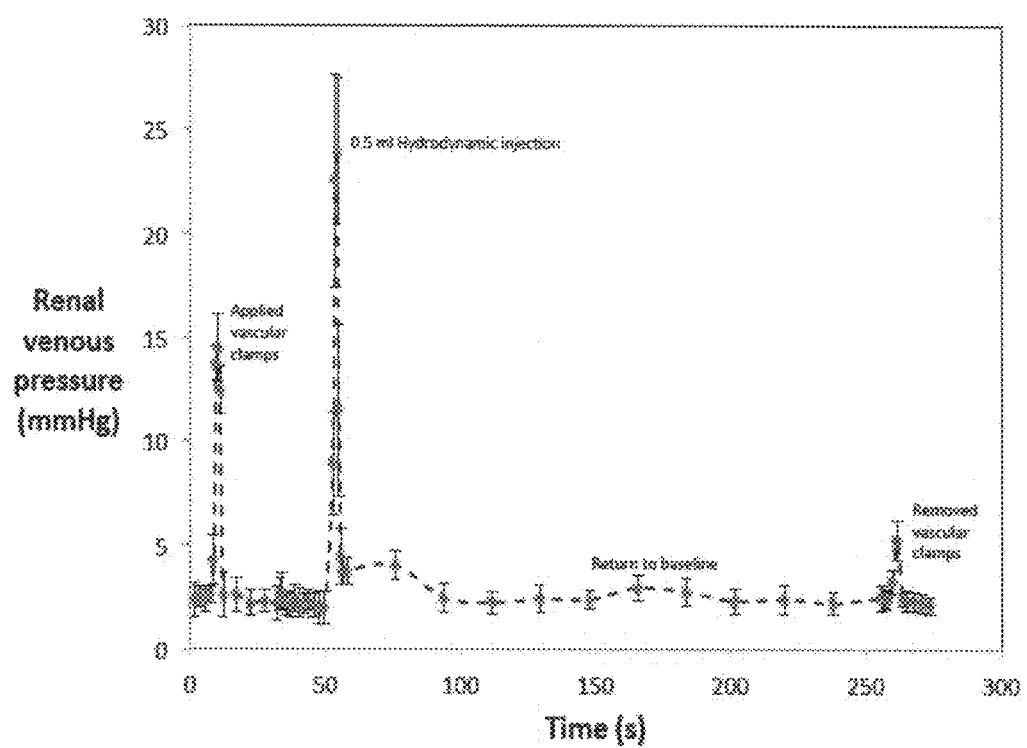
FIG. 10. A measure of the changes in venous pressure that occur throughout a hydrodynamic injection (with vascular clamps) of 0.5 ml solution into the left renal vein of a live rat.

The kidneys were imaged within 20 minutes after these fine-needle injections. In this case the inventors observed widespread distribution of the dextrans in vivo (FIG. 8). Remarkably, this pressurized injection facilitated robust and widespread apical and basolateral (FIG. 8) distribution and cellular internalization of albumin, and large molecular weight TRITC and FITC dextran molecules within tubular epithelial cells in a fashion similar to the incorporation of low molecular weight dextran molecules into proximal tubular cells (FIG. 8D).

The inventors also observed that albumin and large molecular weight dextran molecules were uncharacteristically able to access the tubule lumen at high concentrations after being delivered to the kidney via hydrodynamic injections (FIG. 8C). Similarly, when 150 kDa molecules, were introduced into the bloodstream prior to hydrodynamic injection of saline, they were internalized within tubular epithelial cells. Nevertheless, this atypical access for large molecular weight dextran molecules to tubule lumens and tubular epithelial cells, was transient and appeared to only occur for molecules present at the time of the hydrodynamic injection process, as 150 kDa dextran molecules infused via the jugular vein approximately 20-30 minutes after a hydrodynamic pressurized injection of saline remained confined to the vasculature (FIG. 8F).

G. Parameters Related to Renal Transformation

Figure 15:
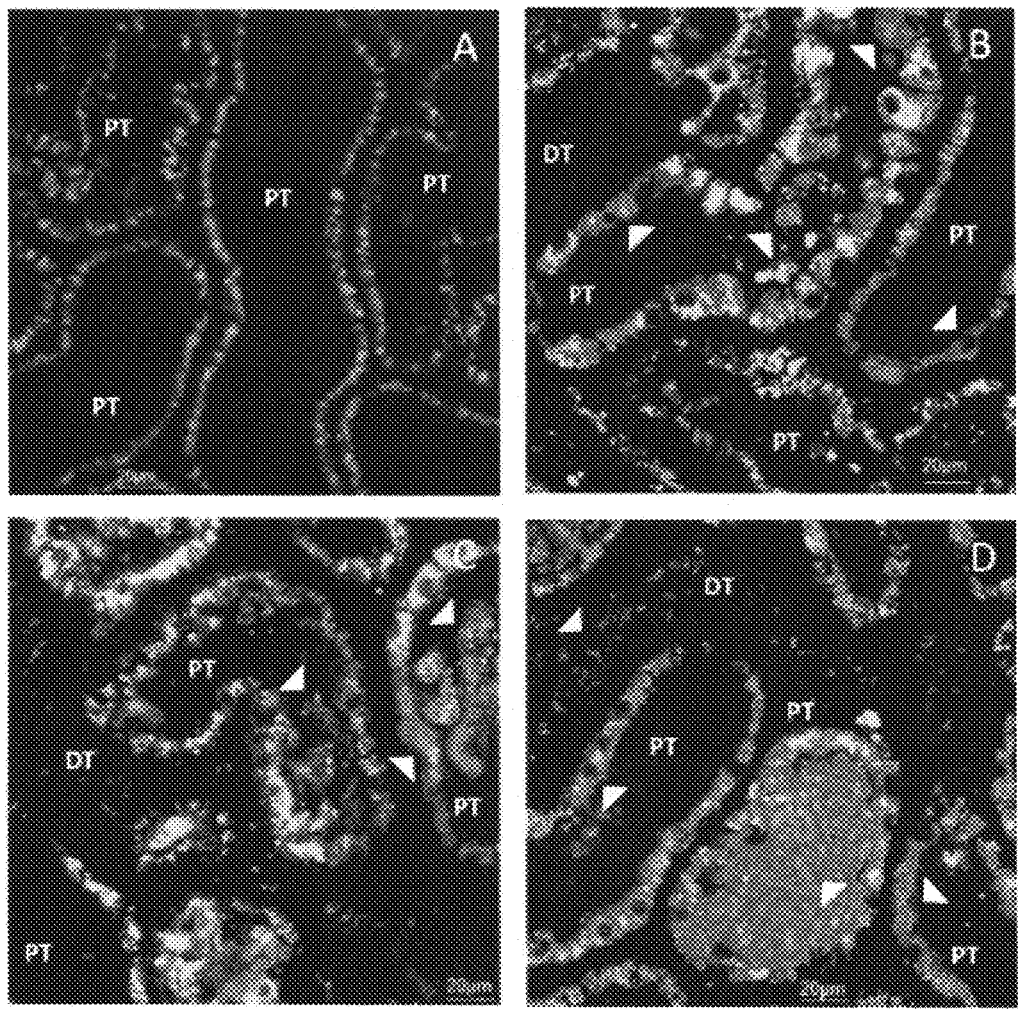
FIG. 15A-FIG. 15D. Fluorescent microscopic images taken from a live rat with moderate ischemia/reperfusion injury 3 days after the initial insult: (A) image taken from a rat that did not receive any transgene or saline treatment. Structural damage can be seen within proximal tubules (PT) by debris within tubule lumens; (B), (C) and (D) images taken from separate rats that were subjected to hydrodynamic transgene delivery of Actin-GFP plasmids 24 hours after a 45 minute bilateral renal clamp. Enhanced transgene-based fluorescence can be seen within intact proximal tubule (PT) epithelial cells and within the lumens of occluded tubules (arrowheads). Again, deformed nuclei within proximal (PT) and distal tubules (DT), and the vasculature (arrows) are hallmarks of apoptosis, which are expected with this ischemia/reperfusion injury. Red and green pseudo-colors are merged in these images to differentiate between transgene and innate tissue fluorescence signals.

In order to characterize parameters related to effective transformation, the inventors recorded changes in renal venous pressures generated during the hydrodynamic injection procedure in the renal vein of live rats. From these measurements, the inventors observed that the application and removal of the vascular clamps produced small transient changes in renal pressure. The hydrodynamic fluid delivery produced pressure responses that generally lasted the duration of the infusions. Overall renal venous pressures increased by up to 25 mmHg (FIG. 15).

This implied that hydrodynamic injections generated significant, yet transient increases in regular renal venous and peritubular capillary pressures.

The inventors next examined the conditions required to inject transgenes at infusion rates lower than that advised for hydrodynamic delivery. The inventors performed 2- and 4-minute long injections. These comparably low infusion rate injections increased periods of venous cannulation, and did not produce significant changes in venous pressure.

Figure 14:
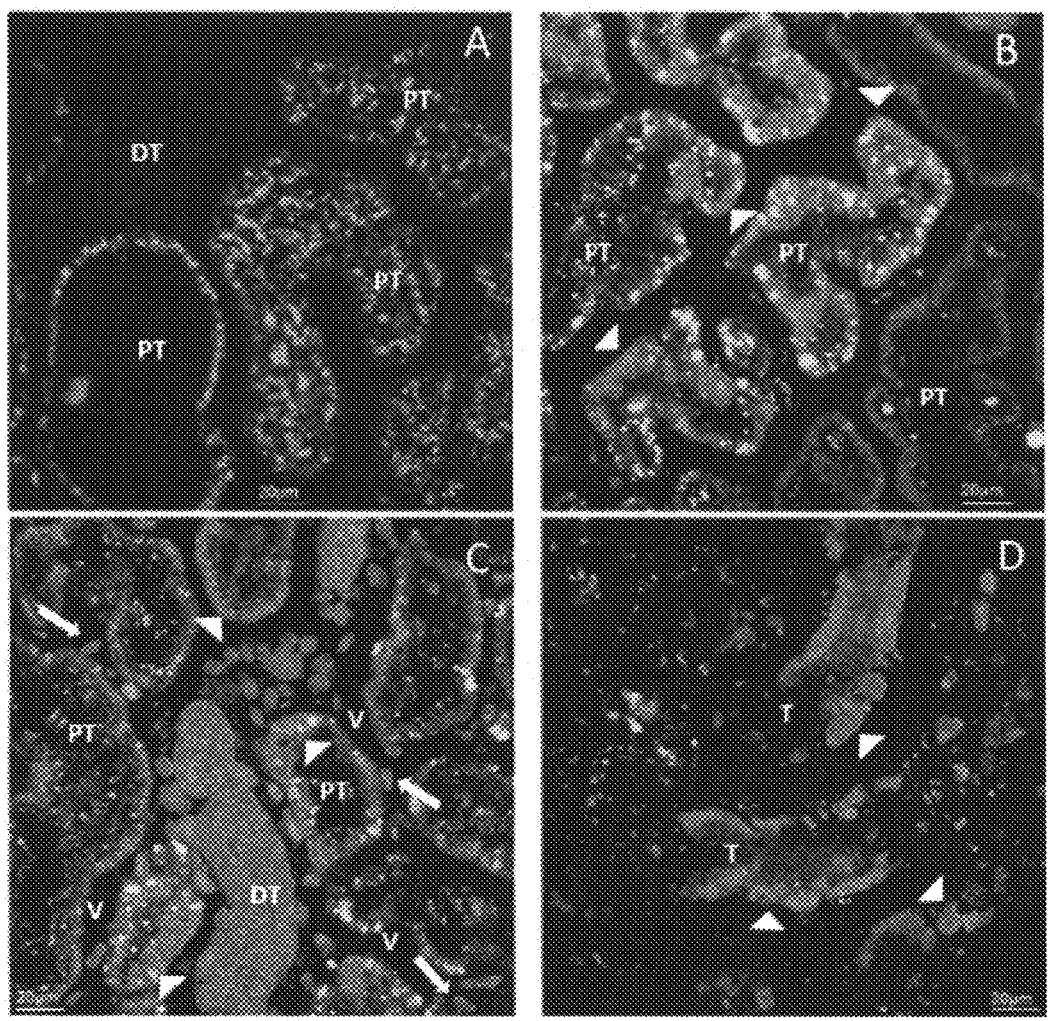
FIG. 14A-FIG. 14D. Fluorescent microscopic images taken from a live rat with moderate ischemia/reperfusion injury 3 days after the initial insult: (A) image taken from a rat that did not receive any transgene or saline treatment. Structural damage can be seen within proximal tubules (PT) by debris within tubule lumens; (B), (C) and (D) images taken from separate rats that were subjected to hydrodynamic transgene delivery of Actin-GFP plasmids 1 hour after a 45 minute bilateral renal clamp. Enhanced transgene-based fluorescence can be seen within intact proximal tubule (PT) epithelial cells and within the lumens of occluded tubules (arrowheads). In (C) Hoechst 33342 was added to label nuclei. Red and green pseudo-colors are merged in these images to differentiate between transgene and innate tissue fluorescence signals. In certain cases the injury was so severe that is was difficult to identify specific renal segments as seen in (D).

Interestingly, these lower injections rates also generated successful transgene expression, see FIG. 14. However, as previously mentioned, 4-minute long injections allowed prolonged entry of the 30-gauge needle into the venous cavity. This resulted in extensive bleeding and beyond 15 minutes of vessel occlusion to induce hemostasis. According to literature, this insult is known to produce acute kidney injury, which is characteristic of the observed in vivo and in vitro tissue damage. These data suggests that lower hydrodynamic infusions rates can generate significant renal injury.

Example 2

Acute Kidney Injury Therapy

All renal injuries were generated using micro-serrefines. Rats were anesthetized from intraperitoneal injections of 50 mg/kg pentobarbital, and then placed on a heating pad to maintain normal physiological body temperature. Once fully sedated, their abdomen was shaved, cleaned with betadine solution and midline incisions were created to isolate the renal pedicles. Thereafter, bilateral renal pedicle clamps were used to occlude blood flow for two specific periods: 10-15 and 30-45 minutes. These damp times correspond to mild, acute kidney injuries respectively. After each period of ischemia, the micro-serrefines were removed to reinstate renal blood flow and the animals were prepared to receive hydrodynamic transgene delivery 60 minutes and 24 hours (timeframe for maximal injury with AKI) after ischemia/reperfusion injury. In the case of the 24-hour injection time point, each rat was allowed to recover from the effects of the anesthetic. After isolating the renal veins in sedated normal and injured rats, the inventors elevating this vein with a silk loop and clamped the renal artery and then the vein. A 0.5 ml transgene solution (transgenes suspended in saline were used to determine if the inventors could simultaneously induce exogenous protein expression in live animals, while providing a therapeutic benefit from the fluid injection) or saline was then rapidly injected into the vein, distal to the clamp. Again after this injection, pressure was applied to the injection site for approximately three minutes. The inventors then removed the venous clamp, followed by the arterial clamp, and prepared the animal for recovery. The inventors collected sera from these animals across a period of 72 hours to investigate the changes in creatinine that may be obtained using hydrodynamic fluid delivery. From the results, the inventors determined that hydrodynamic fluid delivered at the maximal time of injury (24 hours) returned serum creatinine normal levels in rats with AKI. In comparison, animals with AKI that did not receive any intervention remained with elevated creatinine levels as anticipated.

Moreover, serum creatinine levels in normal rats were not affected by hydrodynamic delivery, this result suggests that the hydrodynamic fluid delivery process does not appear to have a debilitating affect on overall renal function. Similarly, in rats with mild ischemia there was also no recorded increase serum creatinine values, as again anticipated.

| Experimental Model | Mean Creatinine Day 0 | Mean Creatinine Day 1 | Mean Creatinine Day 2 | Mean Creatinine Day 3 | Mean Creatinine Day 4 | Mean Creatinine Day 5 |
|---|---|---|---|---|---|---|
| Normal | 0.4 | 0.4 | 0.5 | 0.4 | 0.4 | 0.3 |
| AKI | 0.47 | 3.97 | 3.39 | 2.85 | 1.5 | 0.6 |
| AKI + HD 1 hour post injury | 0.35 | 3.9 | 3.2 | 1.95 | 1.1 | 0.55 |
| AKI + HD 24 hours post injury | 0.37 | 2.92 | 2.4 | 1.54 | 0.57 | 0.5 |

Figure 18:
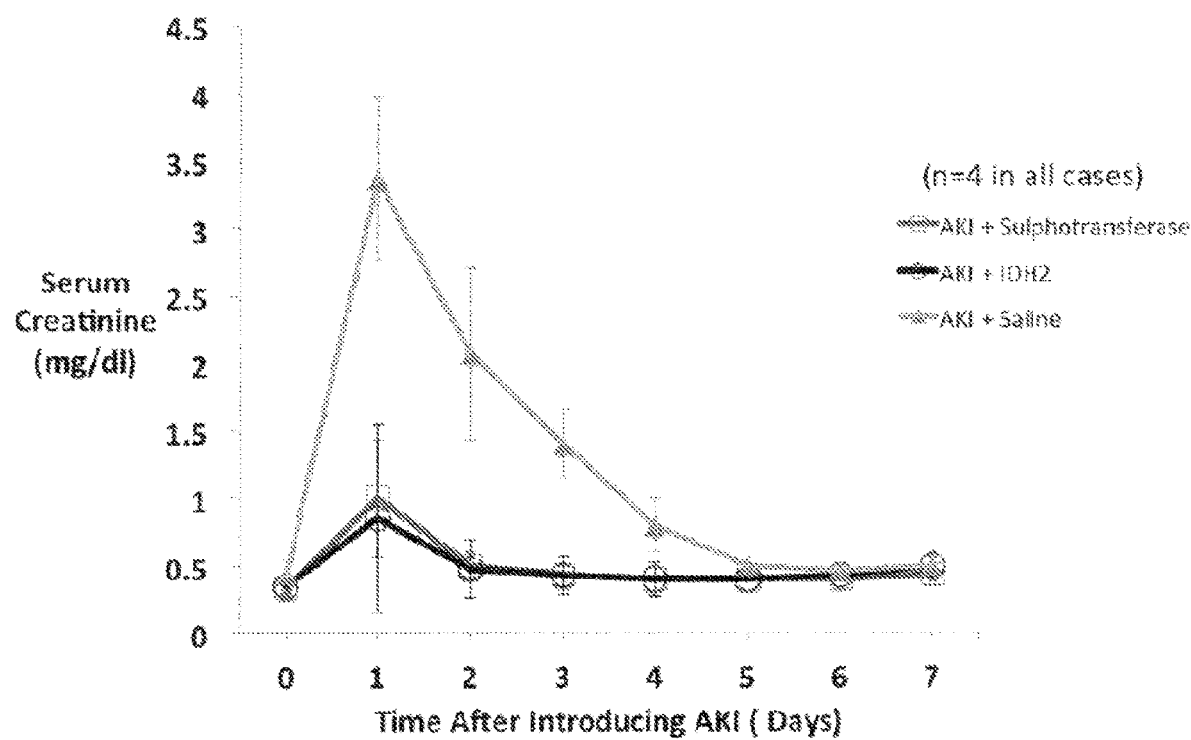
FIG. 18. Rats Hydrodynamically treated with plamids encoding mitochondrial proteins appear to be less susceptible to acute ischemia-reperfusion injury.
Figure 19:
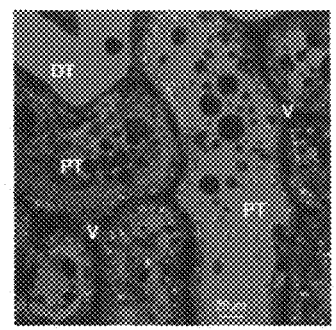
FIG. 19. An intravital multiphoton micrograph of Texas Red labeled albumin in live rat proximal (PT) and distal (DT) tubules and the vasculature (V), approximately 20 minutes it after it hydrodynamically delivered through the left renal vein of a rat. This 1 ml fluorescent solution was injected at an approximate rate of 0.1 ml/s, using a PESO catheter that was inserted into the left renal vein. The venous catherization resulted in vasculature constriction, reduced luminal surface area of PT epithelial cells, and fluorescent vesicles and non-fluorescent blebs within tubule lumens. The image, taken with a 60× water objective lens, presents a merger of signals derived from tissue auto fluorescence (green pseudo-color signal) and dye-based fluorescence (red pseudo-color signal).
Figure 20:
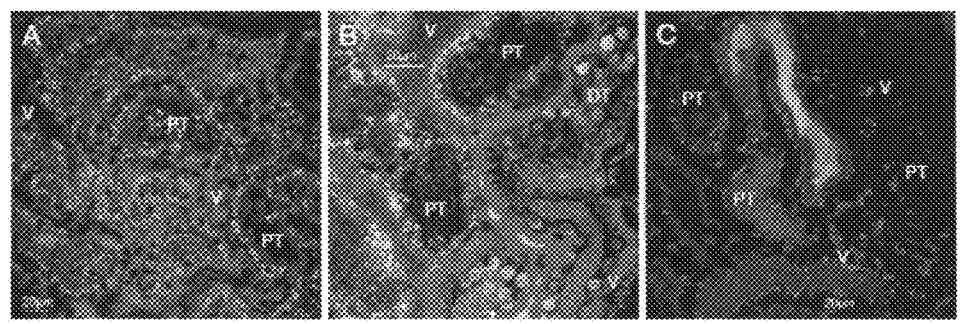
FIG. 20A-FIG. 20C. Intravital multiphoton micrographs taken within 20 minutes after the simultaneous infusion of low (either 3 kDa Cascade Blue or 4 kDa FITC) and large (150 kDa TRITC) dextrans. These data illustrate the effects that result from varying the hydrodynamic injection rate and method (lower infusion volume and added vascular clamping). Each retrograde injected was performed using a 30-gauge needle. Signs of intact nephron structure and function are observed in image: (A) 10-second long hydrodynamic injections, without vascular clamps, of 1 ml solution containing 3 kDa Cascade Blue and 150 kDa TRITC dextrans, and (B) 5-second long injections (injection rate 0.1 ml/s), with vascular clamps, of 0.5 ml solution containing 4 kDa FITC and 150 kDa TRITC dextrans (Hoechst was added to label nuclei). In comparison, image (C) outline that 4-minute long injections (injection rate 0.0042 ml/s), without vascular clamps, of 1 ml saline containing 3 kDa Cascade Blue and 150 kDa dextrans, produce vascular constriction, tubular blockage and filtration of the large 150 kDa as observed in FIG. 1. These are the mergers of blue, green and red pseudo-colors originating from the low and large molecular weight dextrans.
Figure 21:
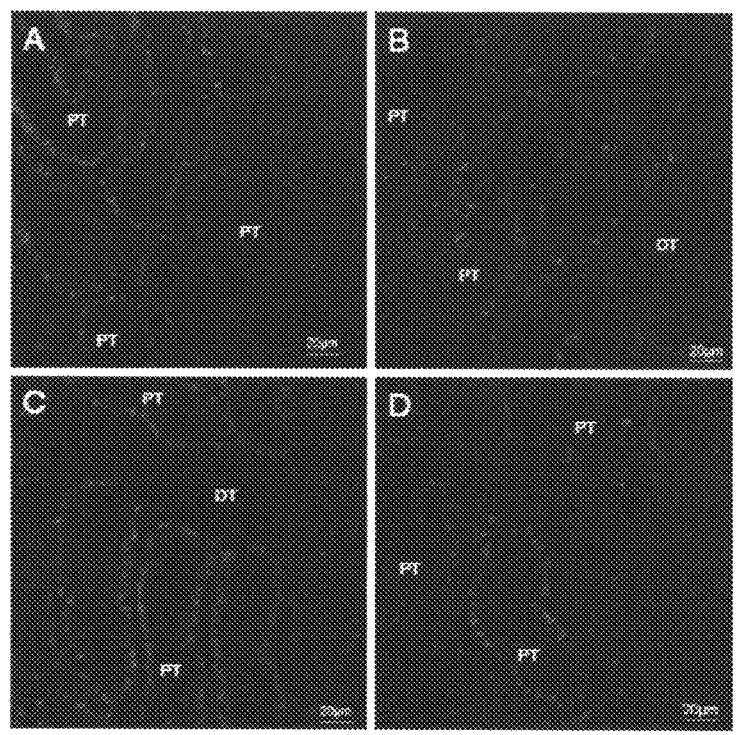
FIG. 21A-FIG. 21D. Live rat kidney tubules micrographs obtained from animals prior to and 3 days after they received sham and hydrodynamic injections of saline: (A) rat kidney imaged prior to a sham injection, (B) kidney imaged 3 days after receiving a sham injection, (C) rat kidney imaged prior to a hydrodynamic injection of saline, (D) kidney imaged 3 days after receiving a hydrodynamic injection of saline.
Figure 22:
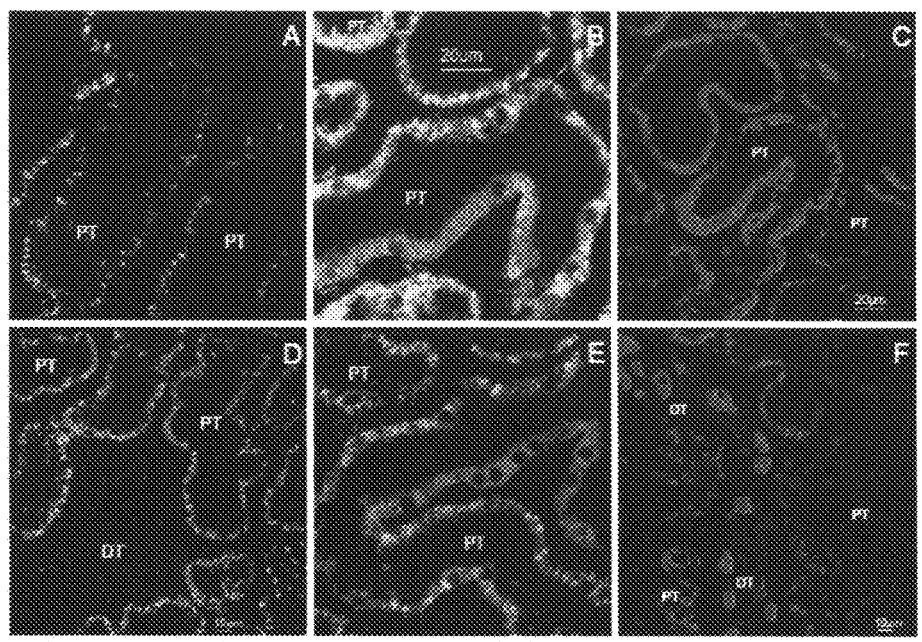
FIG. 22A-FIG. 22F. Transgene expression recorded in live Sprague Dawley rats that received hydrodynamic injections (augmented with vascular clamps) of EGFP and EGFP-Tubulin plasmid vectors. Image (A), was taken from a rat prior to its treatment with pEGFP naked plasmid vectors, and (B) and (C) were taken from that animal 3 days after it was treated with pEGFP naked plasmid vectors. Similarly, image (D), was taken from another rat prior to its treatment with pEGFP-Tubulin naked plasmid vectors, and (E) and (F) were taken from that animal 3 days after it was treated with pEGFP-Tubulin naked plasmid vectors. Transgene expression can be seen within live distal tubules (DT), image (F), and proximal tubules (PT), images (B), (C), and (E). Red and green pseudo-colors were merged to differentiate between ECFP and autofluoresence signals.
Figure 23:
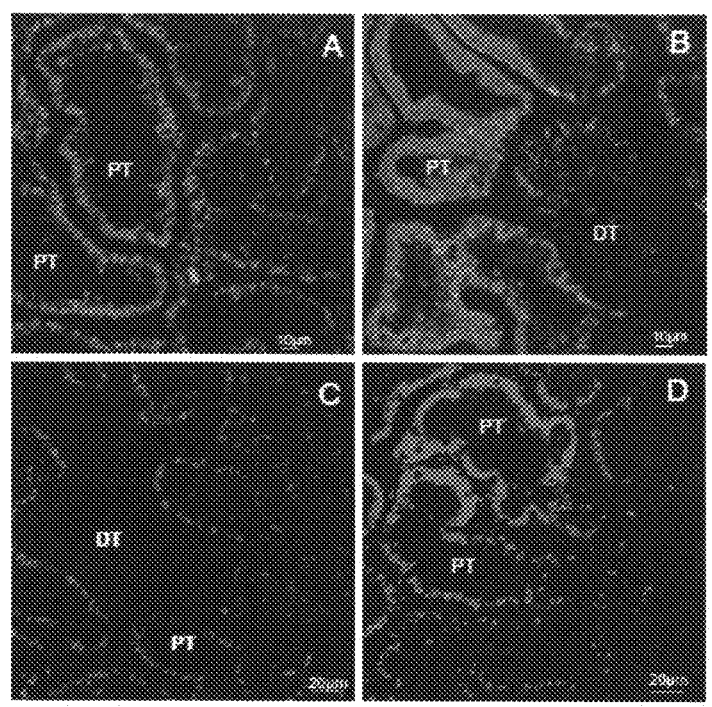
FIG. 23A-23D. A comparison of fluorescent micrographs taken from live Sprague Dawley rats that received hydrodynamic injections of GFP-Actin and RFP-Actin adenovirus vectors: image (A) was recorded in a rat prior to transgene delivery of GFP-Actin adenovirus vectors; image (B) was taken from that animal 3 days post delivery of GFP-Actin adenovirus vectors; image (C) was recorded prior to transgene delivery of RFP-Actin adenovirus vectors; and image (D) was taken from that animal 3 days post the delivery of RFP-Actin adenovirus vectors. Red and green pseudo-colors were merged to distinguish between fluorescence (GFP and RFP) and autofluoresence signals.
Figure 24:
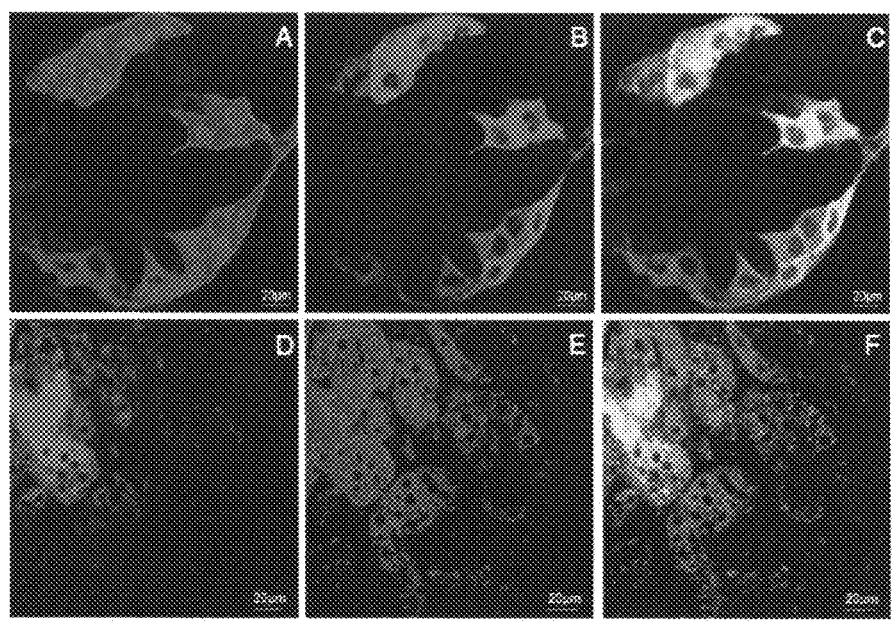
FIG. 24A-24F. Simultaneous transgene expression observed in MDCK cells and Sprague Dawley rat kidneys with both GFP-Actin and RFP-Actin adenovirus vectors. The cells were imaged 1 day after incubation with the adenovirus vectors, with the ex vivo kidney images were taken from within the superficial cortex of a freshly excised whole kidney. The kidney was harvested from a rat 3 days after it was injection of the adenovirus vectors, and was imaged within 5 minutes after its excision. Red and green pseudo-colors were merged to distinguish between fluorescence (GFP and RFP) and autofluoresence signals, and highlight regions with co-transgene expression.
Figure 25:
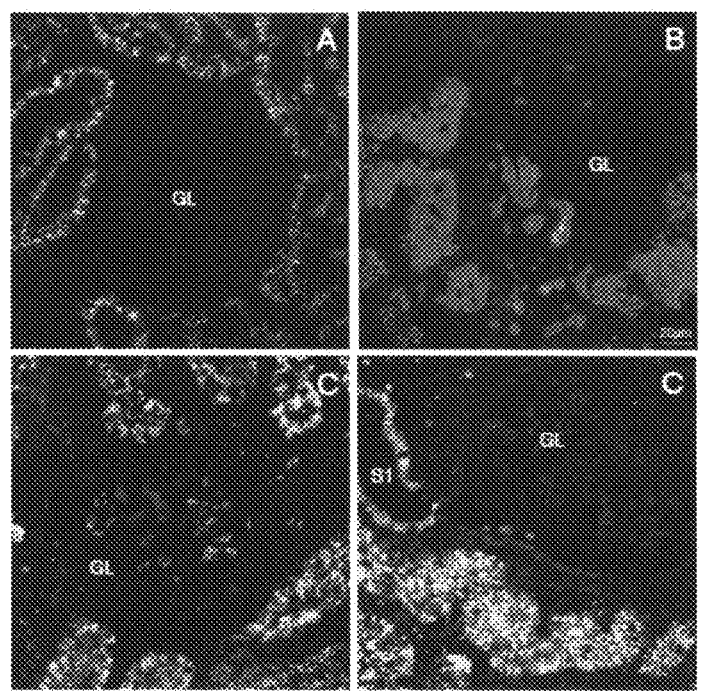
FIG. 25A-FIG. 25D. A comparison of hydrodynamic-based transgene expression in live glomeruli using adenovirus and plasmid vectors in various rats 3 and 7 days post transgene delivery: (A) image of a glomerulus taken from a kidney treated with saline (control) 3 days post hydrodynamic injection; (B) image of a glomerulus taken from a kidney treated with GFP-Actin adenovirus vectors 7 days post hydrodynamic injection; and (C) and (D) images of glomeruli taken from kidneys treated with EGFP-Actin plasmid vectors 3 days post hydrodynamic injection. Prior to obtaining images (C) and (D), 150 kDa TRITC dextran solutions were infused through the jugular veins to outline the glomerular capillaries and supporting vasculature and investigate structural and functional capacities of nephron segments after the transgene delivery process. Red and green pseudo-colors were merged to distinguish between GFP and autofluoresence signals.
Figure 26:
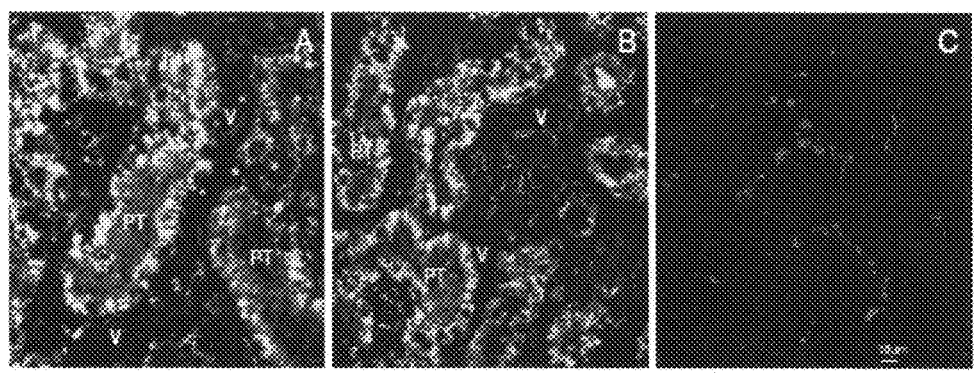
FIG. 26A-FIG. 26C. Transgene expression in observed in cells surrounding the vasculature (A) and (B), and (C) adipose tissue of the prirenal fat. The images were taken close to the renal capsule in a rat 3 days after it received a hydrodynamic injection of EGFP-Actin plasmid vectors. A 150 kDa TRITC dextran solution were infused through jugular veins to outline vasculature (V). Red and green pseudo-colors were merged to distinguish between fluorescence (GFP and RFP) and autofluoresence signals.

In addition, the inventors used pressurized retrograde renal vein injections to deliver mitochondrial genes IDH2 and suphotransferase to normal rats and waited for a period of seven days. Moderate ischemia-reperfusion injury was then induced using the bilateral renal clamp model. The serum creatinine levels were monitored before and after inducing the injury. It was determined that rats that received hydrodynamic injections of approximately 600 µg of the plasmids were resistant to acute kidney injury that was generated by moderate ischemia reperfusion. See FIG. 18.

Example 3

Ischemia Therapy

Ischemia-reperfusion injuries remain a significant clinical problem, as approximately 25% of ICU patients experience acute kidney injury (AKI). These patients have increased risk of end-stage renal failure, and mortality. Therapy of AKI depends on the identification and treatment of its underlying cause(s), yet current treatment regimens are mainly supportive. In the absence of hypervolemia, intravenous fluid delivery is oftentimes the first course of treatment. This standard approach is employed to prevent or eliminate volume depletion, ameliorate tubular blockage, dilute nephrotoxin, facilitate diuresis and restore normal GFR. In this study, the inventors investigated the therapeutic potential of a relatively low volume (0.5 ml) hydrodynamic isotonic fluid delivery to the left renal vein 1 and 24 hours after inducing moderate ischemia-reperfusion injury. Strikingly, from only the fluid delivered at the 24-hour mark, the inventors observed substantial and statistically significant (p-value=0.02) decrease in serum creatinine as compared to control untreated animals. The creatinine levels were also significantly different (p-value=0.03) from those obtained after fluid delivery at the 1 hour time point. Additionally, hydrodynamic fluid delivery provided at the 24 hour mark mediated a return to baseline serum creatinine levels within 4 days of the initial insult. The potential therapeutic benefit observed in these results provides an exciting platform to facilitate the future management of ischemia-reperfusion injuries using in a single infusion technique.

Renal injury was generated using renal pedicle cross clamps. Rats were anesthetized from intraperitoneal injections of 50 mg/kg pentobarbital, and then placed on a heating pad to maintain normal physiological temperature. Using a standard model to generate renal injury, bilateral renal pedicle clamps were applied to occlude blood flow for periods of 10-15 and 30-45 minutes. These clamp period correspond to mild and moderate/acute kidney injuries respectively. At the end of each period, the clamps were removed to reinstate renal blood flow and the animals were prepared to receive hydrodynamic transgene delivery at either 1 or 24 hours after ischemia/reperfusion injury (the 24 hour time point corresponds to the period of maximal damage in AKI). After isolating the left renal vein in each sedated rat, the inventors elevated the vein with a 4-0 silk loop, and clamped the renal artery and then the vein. The left kidney was chosen over the right vein primarily because it is easier to conduct the necessary surgical manipulations on this site in the mammal. A 0.5 ml transgene solution was then rapidly injected into the vein, distal to the clamp. Pressure was then applied to the injection site for approximately three minutes to induce hemostasis. The inventors then removed the venous clamp, followed by the arterial clamp, and prepared the animal for recovery.

Figure 11:
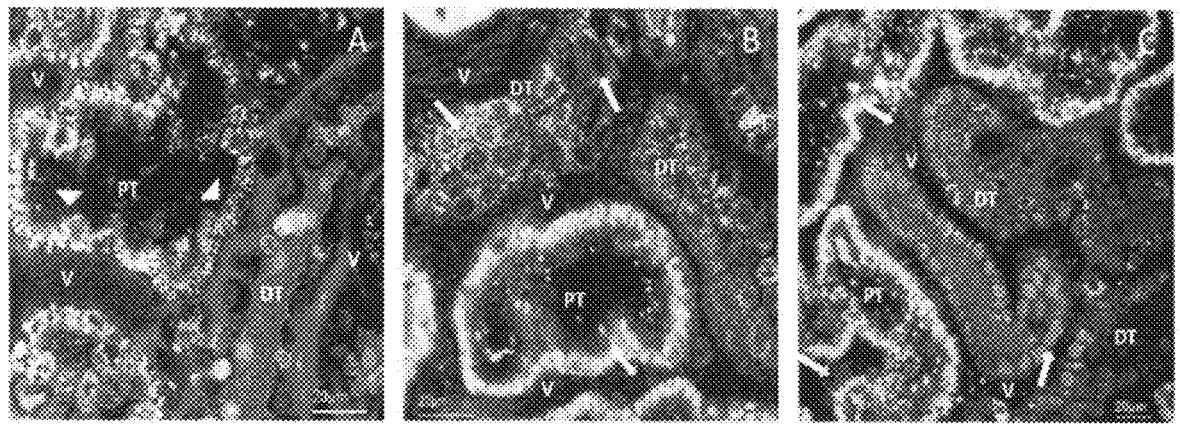
FIG. 11A-FIG. 11C. Intravital multiphoton micrographs, taken with a 60× objective, from two live rats within 20 minutes of receiving hydrodynamic infusions of 0.5 ml saline containing 4 kDa FITC and 150 kDa TRITC dextrans, and Hoechst 33342 in (A) a normal rat; and (B) and (C) a rat with significant renal injury (hydrodynamic injection was given 1 hour after a 45 minute bilateral renal occlusion). In (A), 1.5× digital zoom, we observe intense TRITC signals confined to the vasculature, FITC dextran molecules that appear to bound brush borders (arrowhead) and as endocytosed puncta within proximal tubule (PT) epithelial cells, and accumulation of the FITC dye within the lumens of the distal tubules (DT). These obsercations provide evidence of intact structural and functional renal capacities and widespread delivery of exogenous materials. In comparison, the relatively lower signal from the TRITC dextran within the vasculature (V) in (B) 1.5× zoom and (C) signifies a reduction in renal blood flow, deformed and denatured nuclei within PTs, DTs, and the vasculature (arrows)—hallmarks of apoptosis, and reduced level of renal filtration (reduced concentration of FITC molecules and blebs within distal tubule lumens), are characterized by sever ischemia/reperfusion injuries. Nevertheless, there is still widespread uptake of the exogenous materials in this injury model. Red, green and blue pseudo-colors are merged in show the presence of each probe. All images present a merger of signals derived from Hoechst 33342 labeled nuclei (blue pseudo-color signal) tissue auto fluorescence (green pseudo-color signal) and dye-based fluorescence (re pseudo-color signal).

Prior to attempting hydrodynamic transgene delivery in rats with any form of renal ischemia/reperfusion injury, the inventors first determined whether it was possible to use this technique to successfully deliver exogenous substances to injured kidneys. To answer this question, the inventors compared the results obtained from the hydrodynamic delivery of fluorescent dextrans in injured kidneys to that in normal kidneys. Intravital micrographs, data presented in FIG. 11, were taken from both groups of rats, within 20 minutes of them receiving hydrodynamic infusions of 0.5 ml saline containing 4 kDa FITC (low molecular weight) and 150 kDa TRITC signals (large molecular weight) dextrans, and 30 ul of Hoechst 33342. The Hoechst 33342 was added to identify cellular nuclei. FIG. 11A illustrates the distribution of the hydrodynamically delivered probes in normal rat kidney. Intense TRITC signals are confined to the vasculature, and FITC conjugated dextrans delineate brush borders of proximal tubules and are observed as internalized puncta within tubular epithelial cells. Moreover, the FITC dye appears more concentrated within the lumen of the distal tubules. These observations are consistent with previously presented data that outline intact structural and functional renal capacities.

Figure 12:
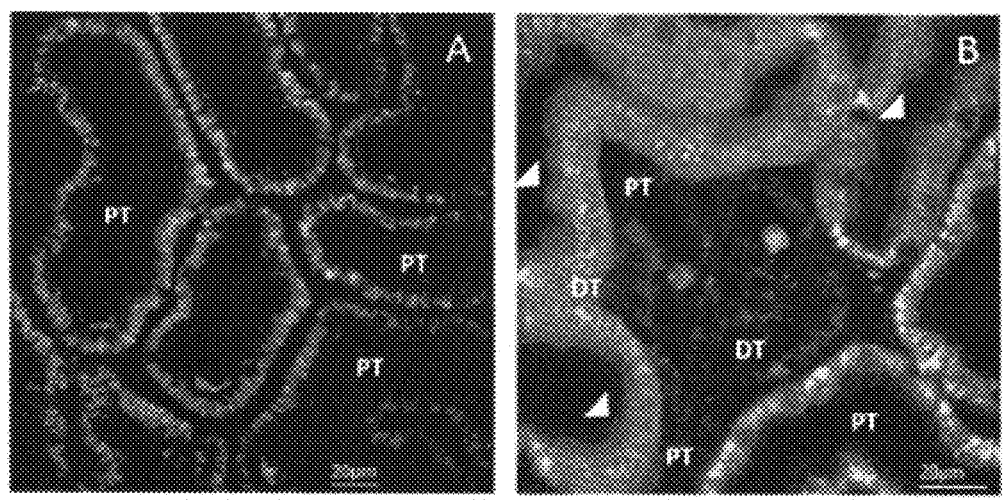
FIG. 12A-FIG. 12B. Intravital multiphoton micrographs taken: (A) before hydrodynamic delivery (tissue autofluoresence), (B) 3 days after hydrodynamic deliver of Actin-GFP plasmids in the same rat (1.5× optical zoom to highlight transgene expression pattern along brush borders). Arrowheads indicate the regions of enhanced transgene-based fluorescence along the brush border of proximal tubule (PT) epithelial cells and within distal tubule epithelial (PT) cells. Red and green pseudo-colors are merged in these images to differentiate between transgene and innate tissue fluorescence signals.
Figure 13:
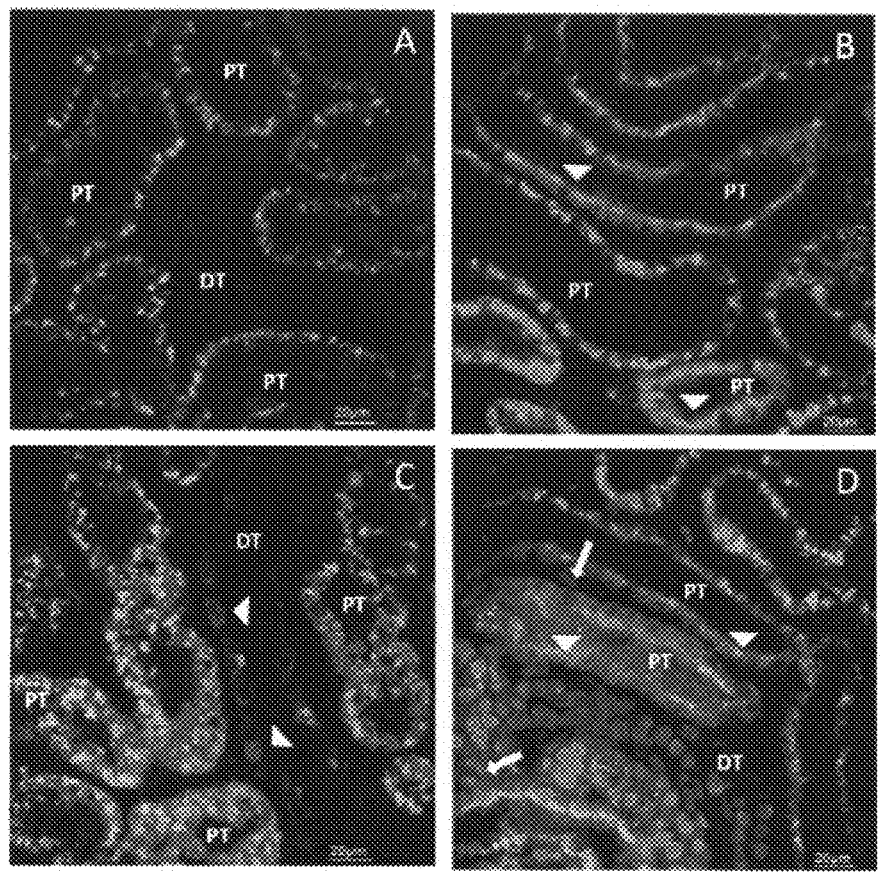
FIG. 13A-FIG. 13D. Multiphoton fluorescent microscopic images taken from a live rat with mild ischemia/reperfusion injury 3 days after the initial insult: (A) image taken from a rat that did not receive any transgene or saline treatment. Structural damage can be seen within proximal tubules (PT) by debris within tubules lumens; (B), (C) and (D) images taken from separate rats that were subjected to hydrodynamic transgene delivery of Actin-GFP plasmids 1 hour after a 15 minute bilateral renal clamp. Enhanced transgene-based fluorescence can be seen within intact proximal tubule (PT) epithelial cells (arrowheads). Again, deformed nuclei within proximal (PT) and distal tubules (DT), and the vasculature (arrowheads) are hallmarks of apoptosis, which are expected with this ischemia/reperfusion injury. Red and green pseudo-colors are merged in these images to differentiate between transgene and innate tissue fluorescence signals.

Using intravital fluorescent multiphoton, microscopy micrographs were then acquired from live rats that received hydrodynamic transgene injections at the time points 1 and 24 hours after inducing mild and acute ischemia/reperfusion injuries. In these micrographs, FIG. 13, transgene-expressed GFP fluorescence is observed within proximal tubule epithelial cells and within the lumens of occluded tubules of live rats that received plasmid injected treatment at both investigated injection time points. The distinctive fluorescent pattern observed along proximal tubule brush borders in normal rats, FIG. 12, was also present in rats with the mild form of injury, FIG. 13. However, this pattern was absent in rats with moderate ischemia/reperfusion injury, as seen in FIGS. 14 and 15. As expected, there was also a substantial disruption to normal renal architecture in the rats that received the moderate form of injury. This made it at times particularly difficult to make morphologic distinctions between proximal and distal tubules, as shown in FIG. 14D.

Figure 16:
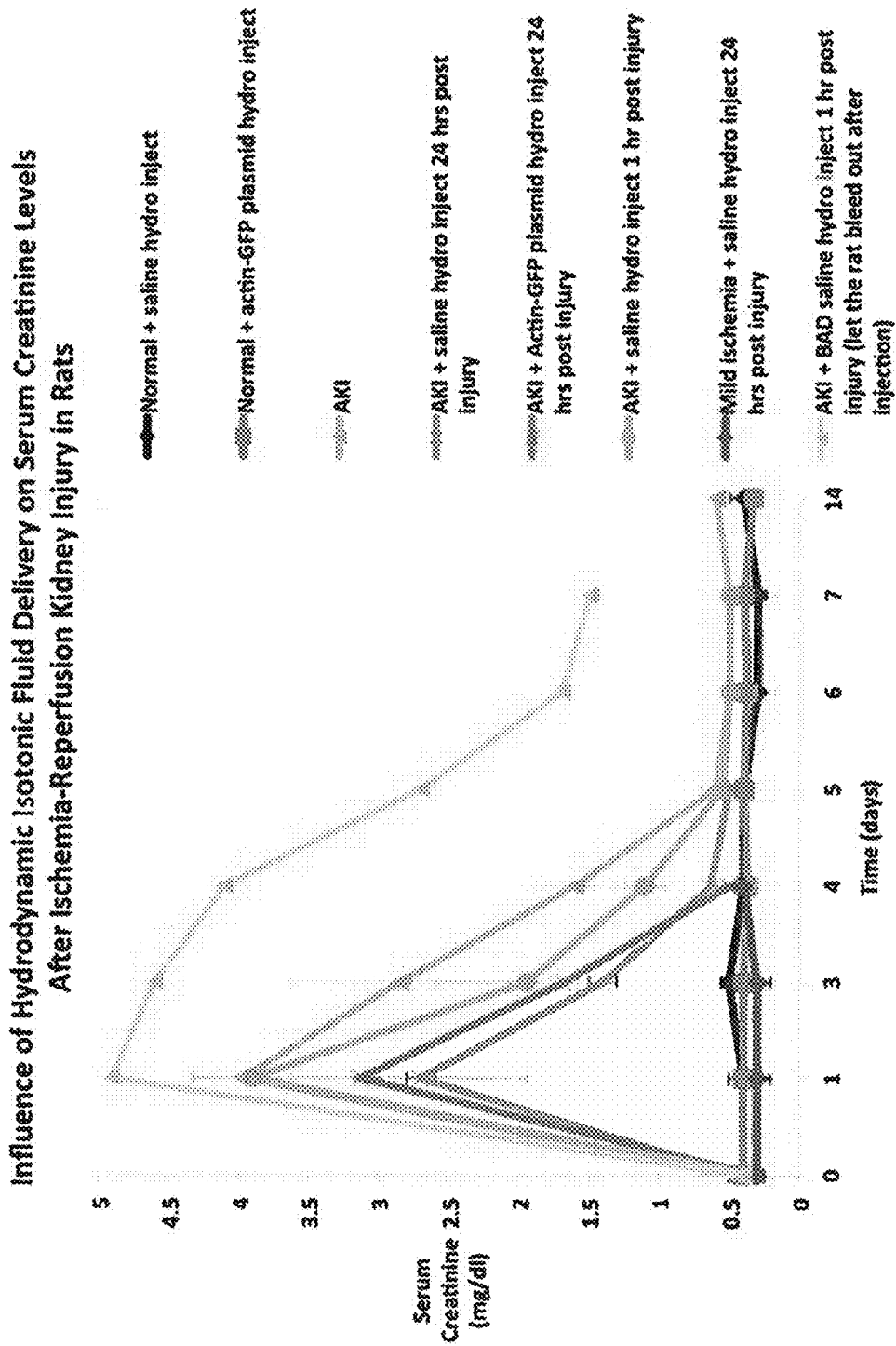
FIG. 16. Influence of hydrodynamic isotonic fluid delivery on serum creatine levels after ischemia-reperfusion kidney injury in rats.
Figure 17:
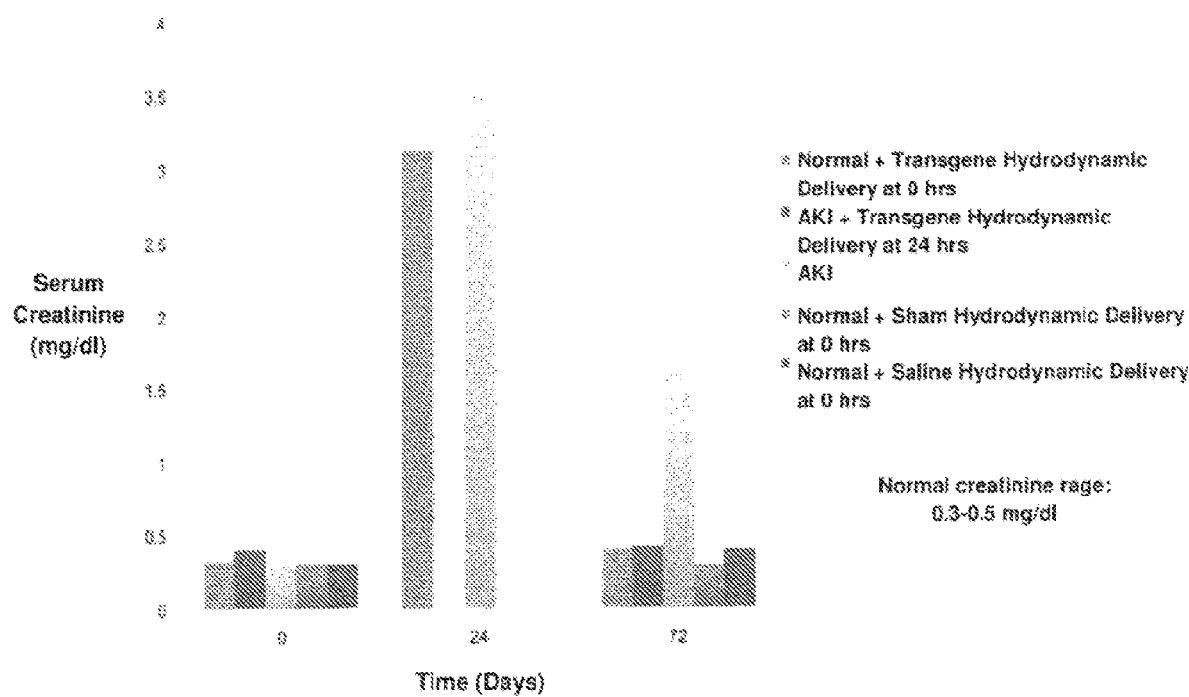
FIG. 17. Hydrodynamic fluid delivery appears to have a therapeutic effect in rats with acute ischemia/reperfusion injury.

Additionally, the inventors estimated the degree of transgene expression in live renal segments by determining the percentage of renal segments (primarily tubules) within a microscopic field that expressed the transgenes. A segment was considered to be transfected as long as at least one of its cells expressed GFP. Thereafter, the inventors averaged this value across 10 adjacent microscopic fields to provide our estimate. This estimation provided a 70-90% transfection efficiency rate in superficial cortex that is accessible by intravital multiphoton microscopy, in both groups of rats with moderate ischemia/reperfusion injuries. These estimated efficiencies were greater than those obtained for normal rats and rats with a mild form of ischemia/reperfusion injury, which ranged from approximately 60-70%, FIGS. 16 and 17.

What is claimed is:

1. A method to treat a mammalian subject having an acute kidney injury, the method comprising:
   occluding the renal vein to the kidney having the acute injury;
   administering a retrograde hydrodynamic injection of a therapeutically effective amount of a fluid consisting of an isotonic saline solution into the occluded renal vein of the subject at a site between the occlusion and the kidney such that the renal venous pressure is increased during the injection;
   waiting, after the retrograde hydrodynamic injection, for a decrease in the renal venous pressure before unoccluding the renal vein;
   unoccluding the renal vein; and,
   measuring the serum creatinine level from a biological sample from the mammalian subject where the biological sample is obtained from the mammalian subject after the retrograde hydrodynamic injection is administered and where the serum creatinine level of the mammalian subject is reduced to the normal, baseline level after the injection is administered.

2. The method according to claim 1, where the administration of the retrograde hydrodynamic injection results in increased peritubular capillary pressure which is maintained during the injection.

3. The method according to claim 1, where the treatment reduces the sluggish microvascular flow in peritubular capillaries.

4. The method according to claim 1, where the time between occluding and unoccluding the renal vein is about three minutes or less.

5. The method of claim 1, where the fluid is administered into the occluded renal vein for a length of time from about 1 second to about 60 seconds.

6. The method according to claim 1, where the fluid is administered 1 day after the acute kidney injury.

7. The method according to claim 1, where the acute kidney injury is an ischemia/reperfusion kidney injury.

8. A method to treat an acute kidney injury in a kidney, the method comprising:
   occluding the renal vein to the kidney having the acute kidney injury;
   delivering a plurality of molecules of a fluid to a tubule lumen of the kidney via the renal vein, wherein the delivering of the molecules comprises administering a retrograde hydrodynamic injection of the fluid into the occluded renal vein at a site between the occlusion and the kidney, the retrograde hydrodynamic injection increasing the renal venous pressure during the injection, and waiting, after the retrograde hydrodynamic injection, for a decrease in the renal venous pressure before unoccluding the renal vein; and
   unoccluding the renal vein.

9. The method of claim 8, where the administration of the retrograde hydrodynamic injection results in decreased serum creatine levels.

10. The method of claim 8, wherein the retrograde hydrodynamic injection is administered for a length of time longer than five seconds and less than 60 seconds.

11. The method of claim 8, wherein the fluid consists of a saline solution.

12. A method to treat an acute kidney injury in a kidney, the method comprising:
   occluding the renal vein to the kidney having the acute kidney injury;
   administering a retrograde hydrodynamic injection of a fluid into the occluded renal vein at a site between the occlusion and the kidney, the retrograde hydrodynamic injection increasing the renal venous pressure during the injection;
   waiting, after the retrograde hydrodynamic injection, for a decrease in the renal venous pressure before unoccluding the renal vein; and
   unoccluding the renal vein.

\* \* \* \* \*